United States Patent
Hartman et al.

(10) Patent No.: US 12,186,358 B2
(45) Date of Patent: Jan. 7, 2025

(54) COMPOSITIONS AND METHODS FOR SUPPORTING IMMUNE HEALTH

(71) Applicant: Plexus Worldwide, LLC, Scottsdale, AZ (US)

(72) Inventors: Michael Hartman, Scottsdale, AZ (US); Lauren Knutsen, Phoenix, AZ (US); Michael Rogowski, Phoenix, AZ (US)

(73) Assignee: Plexus Worldwide, LLC, Scottsdale, AZ (US)

( * ) Notice: Subject to any disclaimer, the term of this patent is extended or adjusted under 35 U.S.C. 154(b) by 0 days.

(21) Appl. No.: 17/674,642

(22) Filed: Feb. 17, 2022

(65) Prior Publication Data

US 2022/0257692 A1    Aug. 18, 2022

Related U.S. Application Data

(60) Provisional application No. 63/150,379, filed on Feb. 17, 2021.

(51) Int. Cl.

| | |
|---|---|
| *A61K 47/46* | (2006.01) |
| *A61K 31/365* | (2006.01) |
| *A61K 31/375* | (2006.01) |
| *A61K 31/7048* | (2006.01) |
| *A61K 31/715* | (2006.01) |
| *A61K 31/716* | (2006.01) |
| *A61K 36/07* | (2006.01) |
| *A61K 36/899* | (2006.01) |
| *A61K 9/48* | (2006.01) |

(52) U.S. Cl.
CPC .......... *A61K 36/899* (2013.01); *A61K 31/365* (2013.01); *A61K 31/375* (2013.01); *A61K 31/7048* (2013.01); *A61K 31/715* (2013.01); *A61K 31/716* (2013.01); *A61K 36/07* (2013.01); *A61K 47/46* (2013.01); *A61K 9/48* (2013.01)

(58) Field of Classification Search
None
See application file for complete search history.

(56) References Cited

U.S. PATENT DOCUMENTS

| | | | |
|---|---|---|---|
| 8,017,162 | B2 | 9/2011 | Shimoda et al. |
| 10,441,602 | B2 * | 10/2019 | Heiman ............... A61P 1/00 |
| 10,736,930 | B2 | 8/2020 | Peltier et al. |
| 10,786,522 | B2 | 9/2020 | Burgos et al. |
| 2009/0196921 | A1 | 8/2009 | Ebel et al. |
| 2010/0021533 | A1 | 1/2010 | Mazed et al. |
| 2011/0268825 | A1 * | 11/2011 | Burgos ............... A61K 31/365 424/732 |
| 2014/0107052 | A1 | 4/2014 | Berry et al. |
| 2016/0024187 | A1 | 1/2016 | Zhu |
| 2017/0028004 | A1 | 2/2017 | Peltier et al. |
| 2020/0281242 | A1 | 9/2020 | Pajitpapan et al. |

FOREIGN PATENT DOCUMENTS

EP    1490080 B1 *  11/2010  ........... A61K 36/899

OTHER PUBLICATIONS

Lin, K.-H., et al., Astaxanthin, a Carotenoid, Stimulates Immune Responses by Enhancing IFN-γ and IL-2 Secretion in Primary Cultured Lymphocytes in Vitro and ex Vivo, Int. J. Mol. Sci. 2016, 17(1).*
Shivembe, A., Ojinnaka, D., Determination of vitamin C and total phenolic in fresh and freeze dried blueberries and the antioxidant capacity of their extracts, Integr Food Nutr Metab, 2017 vol. 4(6): 1-5 (Year: 2017).*
Wu, et al., Characterization and Antioxidant Activity of the Complex of Tea Polyphenols and Oat β-Glucan, J. Agric. Food Chem .2011, 59, 10737-10746 (Year: 2011).*
Shafiur Rahman, M., et al., Stability of vitamin C in fresh and freeze-dried capsicum stored at different temperatures, J Food Sci Technol (Mar. 2015) 52(3):1691-1697.*
Jiang L, Yu Z, Lin Y, Cui L, Yao S, Lv L, et al. Low-molecular-weight polysaccharides from agaricus blazei Murrill modulate the Th1 response in cancer immunity. Oncol Lett. 2018; 15: 3429-3436. doi:10.3892/ol.2018.7794.
Lima Cujo, Cordova Coda, Nóbrega ODT, Funghetto SS, Karnikowski MGDO., Does the *Agaricus blazei* Murill mushroom have properties that affect the immune system? An integrative review. J Med Food. 2011; 14: 2-8. doi:10.1089/jmf.2010.0017.
Lull C, Wichers HJ, Savelkoul HFJ.., Antiinflammatory and immunomodulating properties of fungal metabolites. Mediators Inflamm. 2005;2005: 63-80. doi:10.1155/MI.2005.63.
Ahn W-S, Kim D-J, Chae G-T, Lee J-M, Bae S-M, Sin J-I, et al. Natural killer cell activity and quality of life were improved by consumption of a mushroom extract, *Agaricus blazei* Murill Kyowa, in gynecological cancer patients undergoing chemotherapy. Int J Gynecol Cancer. 2004; 14: 589-594. doi: 10.1111/j.1048-891X.2004. 14403.x.

(Continued)

*Primary Examiner* — H. Sarah Park
(74) *Attorney, Agent, or Firm* — Noblitt & Newson, PLLC

(57) ABSTRACT

Various embodiments provide a method of increasing immunity to a virus in a subject. The method can comprise: administering to the subject one or more effective doses of an immune-enhancing natural-based composition; thereby stimulating increased expression one or more of IFN-γ, IL-1B, IL-6, IL-10, IL-12p40, IL-12p70, and TNF-α; inhibiting replication of the virus inside a cell of the subject, and preventing entry of virus into the cell. The method of increasing immunity can further comprise increasing immunity to an upper respiratory tract viral infection. The upper respiratory tract viral infection can be COVID-19. According to some aspects of the method of increasing immunity, the effective dose of the immune-enhancing natural-based composition comprises: 30-70 mgs of cyanidin-3-glucosides; 40-80 mgs of andrographolides; 75-125 mgs of ascorbic acid; 400-600 mgs of beta glucans; 300-500 mgs of polysaccharides; and 75-125 mgs of a blend of antioxidants.

8 Claims, 9 Drawing Sheets

(56) References Cited

OTHER PUBLICATIONS

Wang Z, Dong B, Feng Z, Yu S, Bao Y., A study on immunomodulatory mechanism of Polysaccharopeptide mediated by TLR4 signaling pathway. BMC Immunol. ???; 2015; 16: 1-9. doi:10.1186/s12865-015-0100-5.

Luo KW, Yue GGL, Ko CH, Lee JKM, Gao S, Li LF, et al. In vivo and in vitro anti-tumor and anti-metastasis effects of Coriolus versicolor aqueous extract on mouse mammary 4T1 carcinoma. Phytomedicine. Elsevier GmbH.; 2014;21: 1078-1087. doi:10.1016/j.phymed.2014.04.020.

Saleh MH, Rashedi I, Keating A.., Immunomodulatory properties of coriolus versicolor: The role of polysaccharopeptide. Front Immunol. 2017;8: 1-12. doi: 10.3389/fimmu.2017.01087.

Ramberg JE, Nelson ED, Sinnott RA., Immunomodulatory dietary polysaccharides: A systematic review of the literature. Nutr J. BioMed Central Ltd; 2010;9: 54. doi: 10. 1186/1475-2891-9-54.

Tsang KW, Lam CL, Yan C, Mak JC, Ooi GC, Ho JC. ,Coriolus versicolor polysaccharide peptide slows progression of advanced non-small cell lung cancer. Respir Med. 2003;97: 618-624. doi: 10.1053/rmed.2003.1490.

Pallav K, Dowd SE, Villafuerte J, Yang X, Kabbani T, Hansen J, et al. Effects of polysaccharopeptide from Trametes versicolor and amoxicillin on the gut microbiome of healthy volunteers: A randomized clinical trial. Gut Microbes. 2014;5. doi:10.4161/gmic.29558.

Nemzer B V., Fink N, Fink B., New insights on effects of a dietary supplement on oxidative and nitrosative stress in humans. Food Sci Nutr. 2014;2: 828-839. doi: 10.1002/fsn3.178.

Wang et al., Dietary Supplementation of Black Rice Anthocyanin Extract Regulates Cholesterol Metabolism and Improves Gut Microbiota Dysbiosis in C57BL/6J Mice Fed a High-Fat and Cholesterol Diet First published: Feb. 12, 2020 https://doi.org/10.1002/mnfr.201900876.

Limtrakul et al., Anthocyanins and Proanthocyanidins in Natural Pigmented Rice and Their Bioactivities, IntechOpen, Phytochemicals in Human Health, accessed Jan. 4, 2021.

Shanshan et al., Anthocyanin-rich extract from black rice (*Oryza sativa* L. Japonica) ameliorates diabetic osteoporosis in rats, Food Funct. Sep. 1, 2019;10(9):5350-5360. doi: 10.1039/c9fo00681h. Epub Aug. 8, 2019.

Xia et al., An Anthocyanin-Rich Extract from BlackRice Enhances Atherosclerotic PlaqueStabilization in Apolipoprotein E-Deficient Mice, The Journal of Nutrition , vol. 136, Issue 8, Aug. 2006, pp. 2220-2225, https://doi.org/10.1093/jn/136.8.2220.

Kamal Patel, Cyanidin, Examine.com Team Last Updated: Jun. 14, 2018.

Nemzer et al., New insights on effects of a dietary supplement on oxidative and nitrosative stress in humans, Food Science & Nutrition 2014; 2(6): 828-839.

Bae et al., Optimized preparation of anthocyanin-rich extract from black rice and itseffects on in vitro digestibility, Food Sci Biotechnol . 2017; 26(5): 1415-1422.

Pedro et al., Extraction of anthocyanins and polyphenols from black rice (*Oryza sativa* L.) by modeling and assessing their reversibility and stability, Food Chemistry 191 (2016) 12-20.

Kim et al., The Effects of a Mixture of Brown and Black Rice on Lipid Profiles and Antioxidant Status in Rats, Annals of Nutrition and Metabolism. Ann Nutr Metab 2006;50:347-353.

Dong et al., Dietary Supplementation of Black Rice Anthocyanin Extract Regulates Cholesterol Metabolism and Improves Gut Microbiota Dysbiosis in C57BL/6J Mice Fed a High-Fat and Cholesterol Diet, Molecular Nutrition & Food Research, Food & Function, First published: Feb. 12, 2020 https://doi.org/10.1002/mnfr.201900876.

Abdel-Aal et al., Anthocyanin composition in black, blue, pink, purple and red cereal grains, J. Agric Food Chem. Jun. 28, 2006;55(13):4696-704.

Lee, Jin Hwan, Identification and quantification of anthocyanins from the grains of black rice (*Oryza satvia* L.) varieties, Food science and biotechnology 2010 v.19 No. 2 pp. 391-397.

Hou et al., Identification of anthocyanins isolated from black rice (*Oryza sativa* L.) and their degradation kinetics, Food Research International 50 (2013) 691-697.

Limtrakul et al., Suppression of Inflammatory Responses by Black Rice Extract in RAW 264.7 Macrophage Cells via Downregulation of NF-kB and AP-1 Signaling Pathways, Jun. 2015—Asian Pacific journal of cancer prevention: APJCP 16(10): 4277-83.

Wallace TC, Giusti MM. Anthocyanins. Adv Nutr. 2015;6: 620-622. doi:10.3945/an.115.009233.

Opinion S. Scientific Opinion on the re-evaluation of 4-hexylresorcinol (E 586) as a food additive. EFSA J. 2014; 12: 1-51. doi:10.2903/j.efsa.2014.3643.

Akbar S. Andrographis paniculata: A review of pharmacological activities and clinical effects. Altern Med Rev. 2011;16: 66-77.

Rana AC, Avadhoot Y. Hepatoprotective effects of Andrographis paniculata against carbon tetrachloride-induced liver damage. Arch Pharm Res. 1991; 14: 93-95. doi: 10.1007/BF02857822.

Handa SS, Sharma A., Hepatoprotective activity of andrographolide against galactosamine and paracetamol intoxication in rats. Indian J Med Res—Sect B Biomed Res Other Than Infect Dis. 1990;92: 284-292.

Calabrese C, Berman SH, Babish JG, Xinfang M, Shinto L, Dorr, A phase I trial of andrographolide in HIV positive patients and normal volunteers. Phyther Res. 2000; 14: 333-338. doi: 10.1002/1099-1573(200008)14:5<333::AID-PTR584>3.0.CO;2-D.

Jacob R Sotoudeh, Vitamin C function and status in chronic disease. Nutr Clin Care. 2002;5: 66-74.

Kuroiwa Y, Nishikawa A, Imazawa T, Kanki K, Kitamura Y, Umemura T, et al., Lack of subchronic toxicity of an aqueous extract of Agaricus blazei Murrill in F344 rats. Food Chem Toxicol. 2005;43: 1047-1053. doi: 10.1016/j.fct.2005.02.007.

Lee IP, Kang BH, Roh JK, Kim JR., Lack of carcinogenicity of lyophilized Agaricus blazei Murill in a F344 rat two year bioassay. Food Chem Toxicol. 2008;46: 87-95. doi: 10.1016/j.fct.2007.07.001.

Hor SY, Ahmad M, Farsi E, Lim CP, Asmawi MZ, Yam MF, Acute and subchronic oral toxicity of Coriolus versicolor standardized water extract in Sprague-Dawley rats. J Ethnopharmacol. 2011;137: 1067-1076. doi: 10.1016/j. jep.2011.07.007.

Barros AB, Ferrão J, Fernandes T. , A safety assessment of Coriolus versicolor biomass as a food supplement. Food Nutr Res. 2016;60. doi: 10.3402/fnr.v60.29953.

Ichikawa H, Ichiyanagi T, Xu B, Yoshii Y, Nakajima M, Konishi T., Antioxidant activity of anthocyanin extract from purple black rice. J Med Food. 2001;4: 211-218. doi: 10. 1089/10966200152744481.

Chen XQ, Nagao N, Itani T, Irifune K, Anti-oxidative analysis, and identification and quantification of anthocyanin pigments in different coloured rice. Food Chem. 2012; 135: 2783-2788. doi: 10.1016/j.foodchem.2012.06.098.

Rózańska D, Regulska-Ilow B., The significance of anthocyanins in the prevention and treatment of type 2 diabetes. Adv Clin Exp Med. 2018;27: 135-142. doi: 10.17219/acem/64983.

Brønnum-Hansen K, Honoré Hansen S., High-performance liquid chromatographic separation of anthocyanins of Sambucus nigra L. J Chromatogr A. 1983;262: 385-392. doi:10.1016/S0021-9673(01)88125-5.

Khoo HE, Azlan A, Tang ST, Lim SM.,. Anthocyanidins and anthocyanins: Colored pigments as food, pharmaceutical ingredients, and the potential health benefits. Food Nutr Res. Taylor & Francis; 2017;61. doi:10.1080/16546628.2017.1361779.

Zhu Y, Sun H, He S, Lou Q, Yu M, Tang M, et al. Metabolism and prebiotics activity of anthocyanins from black rice (*Oryza sativa* L.) in vitro. PLoS One. 2018;13. doi:10.1371/journal.pone.0195754.

Zakay-Rones Z, Varsano N, Zlotnik M, Manor O, Regev L, Schlesinger M, et al. Inhibition of Several Strains of Influenza Virus in Vitro and Reduction of Symptoms by an Elderberry Extract (*Sambucus nigra* L.) during an Outbreak of Influenza B Panama. J Altern Complement Med. 1995; 1: 361-369. doi: 10. 1089/acm.1995.1.361.

Torabian G, Valtchev P, Adil Q, Dehghani F,. Anti-influenza activity of elderberry (*Sambucus nigra*). J Funct Foods. Elsevier; 2019;54: 353-360. doi:10.1016/j.jff.2019.01.031.

(56) References Cited

OTHER PUBLICATIONS

Kinoshita E, Hayashi K, Katayama H, Hayashi T, Obata A. Anti-influenza virus effects of elderberry juice and its fractions. Biosci Biotechnol Biochem. 2012;76: 1633-1638. doi: 10.1271/bbb.120112.

Sekizawa H, Ikuta K, Mizuta K, Takechi S, Suzutani T. Relationship between polyphenol content and anti-influenza viral effects of berries. J Sci Food Agric. 2013;93: 2239-2241. doi:10.1002/jsfa.6031.

Barak V, Halperin T, Kalickman I, V. Barak, T. Halperin IK. The effect of Sambucol, a black elderberry-based, natural product, on the production of human cytokines : I . Inflammatory cytokines Healthy donors blood monocyte cultures Cytokine assays Evaluation of Sambucol 's effect. Eur Cytokine Netw. 2012; 12: 4-7. Available: http://www.alkalinediet.com/pdf/Elderberry/ElderberryAntiViral.pdf%5Cnhttp://www.jle.com/en/print/e-docs/00/01/60/95/article.phtml%5Cnhttp://www.ncbi.nlm.nih.gov/pubmed/11399518.

Frank T, Janßen M, Netzel G, Christian B, Bitsch I, Netzel M. Absorption and excretion of elderberry (*Sambucus nigra* L.) anthocyanins in healthy humans. Methods Find Exp Clin Pharmacol. 2007;29: 525-533. doi:10.1358/mf.2007.29.8.1116309.

Hawkins J, Baker C, Cherry L, Dunne E., Black elderberry (*Sambucus nigra*) supplementation effectively treats upper respiratory symptoms: A meta-analysis of randomized, controlled clinical trials. Complement Ther Med. Elsevier; 2019;42: 361-365. doi:10.1016/j.ctim.2018.12.004.

Xiong WB, Shao ZJ, Xiong Y, Chen J, Sun Y, Zhu L, et al. Dehydroandrographolide enhances innate immunity of intestinal tract through up-regulation the expression of hBD-2. DARU, J Pharm Sci. DARU Journal of Pharmaceutical Sciences; 2015;23: 1-7. doi:10.1186/s40199-015-0119-4.

Guo H, Chang J, Liu B, Gao P, Wei W, Wang D, et al. Andrographolide prevents EV-D68 replication by inhibiting the acidification of virus-containing endocytic vesicles. Front Microbiol. 2018;9: 1-10. doi: 10.3389/fmicb.2018.02407.

Coon JT, Ernst E. Andrographis paniculata in the treatment of upper respiratory tract infections: A systematic review of safety and efficacy. Planta Med. 2004;70: 293-298. doi: 10.1055/s-2004-818938.

Wagner L, Cramer H, Klose P, Lauche R, Gass F, Dobos G. et al., Herbal Medicine for Cough: A Systematic Review and Meta-Analysis. Complement Med Res. 2015;22: 359-368. doi: 10.1159/000442111.

Hu X-Y, Wu R-H, Logue M, Blondel C, Lai LYW, Stuart B, et al. Andrographis paniculata (Chuan Xin Lian) for symptomatic relief of acute respiratory tract infections in adults and children: A systematic review and meta- analysis. Arora R, editor. PLoS One. 2017; 12: e0181780. doi: 10.1371/journal.pone.0181780.

ODS. Vitamin C [Internet]. 2018. Available: https://ods.od.nih.gov/factsheets/VitaminC-HealthProfessional/.

Carr AC, Maggini S., Vitamin C and immune function. Nutrients. 2017;9: 1-25. doi: 10.3390/nu9111211.

Wang H, Fu Z, Han C., The Medicinal Values of Culinary-Medicinal Royal Sun Mushroom (*Agaricus blazei* Murrill). Evid Based Complement Alternat Med. 2013;2013: 842619. doi: 10.1155/2013/842619.

Val CH, Brant F, Miranda AS, Rodrigues FG, Oliveira BCL, Santos EA, ., Effect of mushroom *Agaricus blazei* on immune response and development of experimental cerebral malaria. Malar J. BioMed Central; 2015;14: 1-13. doi: 10.1186/s12936-015-0832-y.

Firenzuoli F, Gori L, Lombardo G.., The medicinal mushroom *Agaricus blazei* murrill: Review of literature and pharmaco-toxicological problems. Evidence-based Complement Altern Med. 2008;5: 3-15. doi: 10.1093/ecam/nem007.

Wang HT, Yang LC, Yu HC, Chen ML, Wang HJ, Lu TJ., Characteristics of fucose-containing polysaccharides from submerged fermentation of Agaricus blazei Murill. J Food Drug Anal. 2018;26: 678-687. doi:10.1016/j.jfda.2017.07.006.

Mizuno M, Morimoto M, Minato KI, Tsuchida H., Polysaccharides from agaricus blazei stimulate lymphocyte T-cell subsets in mice. Biosci Biotechnol Biochem. 1998;62: 434-437. doi: 10.1271/bbb.62.434.

Li Y, Lu X, Li X, Guo X, Sheng Y, Li Y, , Effects of Agaricus blazei Murrill polysaccharides on hyperlipidemic rats by regulation of intestinal microflora. Food Sci Nutr. 2020;8: 2758-2772. doi: 10.1002/fsn3.1568.

\* cited by examiner

COMPOSITIONS AND METHODS FOR SUPPORTING IMMUNE HEALTH

BACKGROUND

With every subsequent cold season, humans are interested in ways to bolster their immune system with the hopes of preventing contraction of seasonal associated illness, or if sick, hoping to boost their innate immunity in order to reduce recovery time. With the advent of the COVID-19 pandemic, humans the world over are increasingly health conscience and eager to find ways to bolster their innate immunity. Currently, promising prophylactic treatments are not available, questions remain related to the different vaccine formulations, and the expectation is the pandemic climate could extend for years. Humans are desperate for natural solutions that can support their general innate immune function.

What is lacking in the marketplace is a nutritional supplement comprising a mixture natural product, which is effective in increasing immunity to viral infections, such as COVID-19. Novel natural-based compositions comprising unique combinations of natural ingredients, which can support general innate immune function to viral infections, are needed. In addition, new methods for supporting immune health using the novel natural-based compositions are needed.

SUMMARY

Various embodiments provide natural-based compositions comprising Cyanidin-3-Glucoside from black rice, a blend of antioxidants, as well as andrographides, prebiotic polysaccharides and beta-glucans from mushrooms.

In some embodiments, the natural-based composition is in the form of tablets, wafer capsules, gel capsules, sticks, sachets, vials, droppers or in injectable form. In some embodiments, the composition contains a mixture of: an extract of black rice; an extra of *andrographis paniculata*; ascorbic acid; an extract of *agaricus blazei*; an extract of *coriolus versicolor*; and at least one antioxidant.

Various embodiments provide a method of increasing immunity to viral infections in human subjects. A method can include administering to the subject the natural-based composition.

Various embodiments provide a method of increasing immunity to a virus in a subject. The method can comprise: administering to the subject one or more effective doses of an immune-enhancing natural-based composition; thereby stimulating increased expression one or more of IFN-γ, IL-1B, IL-6, IL-10, IL-12p40, IL-12p70, and TNF-α; inhibiting replication of the virus inside a cell of the subject, and preventing entry of virus into the cell.

The method of increasing immunity can further comprise increasing immunity to an upper respiratory tract viral infection. The upper respiratory tract viral infection can be COVID-19.

According to some aspects of the method of increasing immunity, the immune-enhancing natural-based composition comprises: cyanidin-3-glucosides in a range from 2% to 6% by weight; andrographolides in a range from 3% to 7% by weight; ascorbic acid is in a range from 9% to 13% by weight; beta glucans is in a range from 38% to 42% by weight; polysaccharides is in a range from 30% to 34% by weight; and at least one antioxidant is in a range from 6% to 10% by weight.

According to some aspects of the method of increasing immunity, the effective dose of the immune-enhancing natural-based composition comprises: 30-70 mgs of cyanidin-3-glucosides; 40-80 mgs of andrographolides; 75-125 mgs of ascorbic acid; 400-600 mgs of beta glucans; 300-500 mgs of polysaccharides; and 75-125 mgs of a blend of antioxidants.

Some embodiments include a nutritional supplement in the form of a single serving of one or more unit dosages. The human edible composition can comprise 5-50 mgs of cyanidin-3-glucosides; 10-100 mgs of andrographolides; 50-500 mgs of ascorbic acid; 100-1000 mgs of beta glucans; 50-500 mgs of polysaccharides; and 50-500 mgs of a blend of antioxidants.

DRAWINGS

The present disclosure will become more fully understood from the description and the accompanying drawings, wherein.

Figure 8:
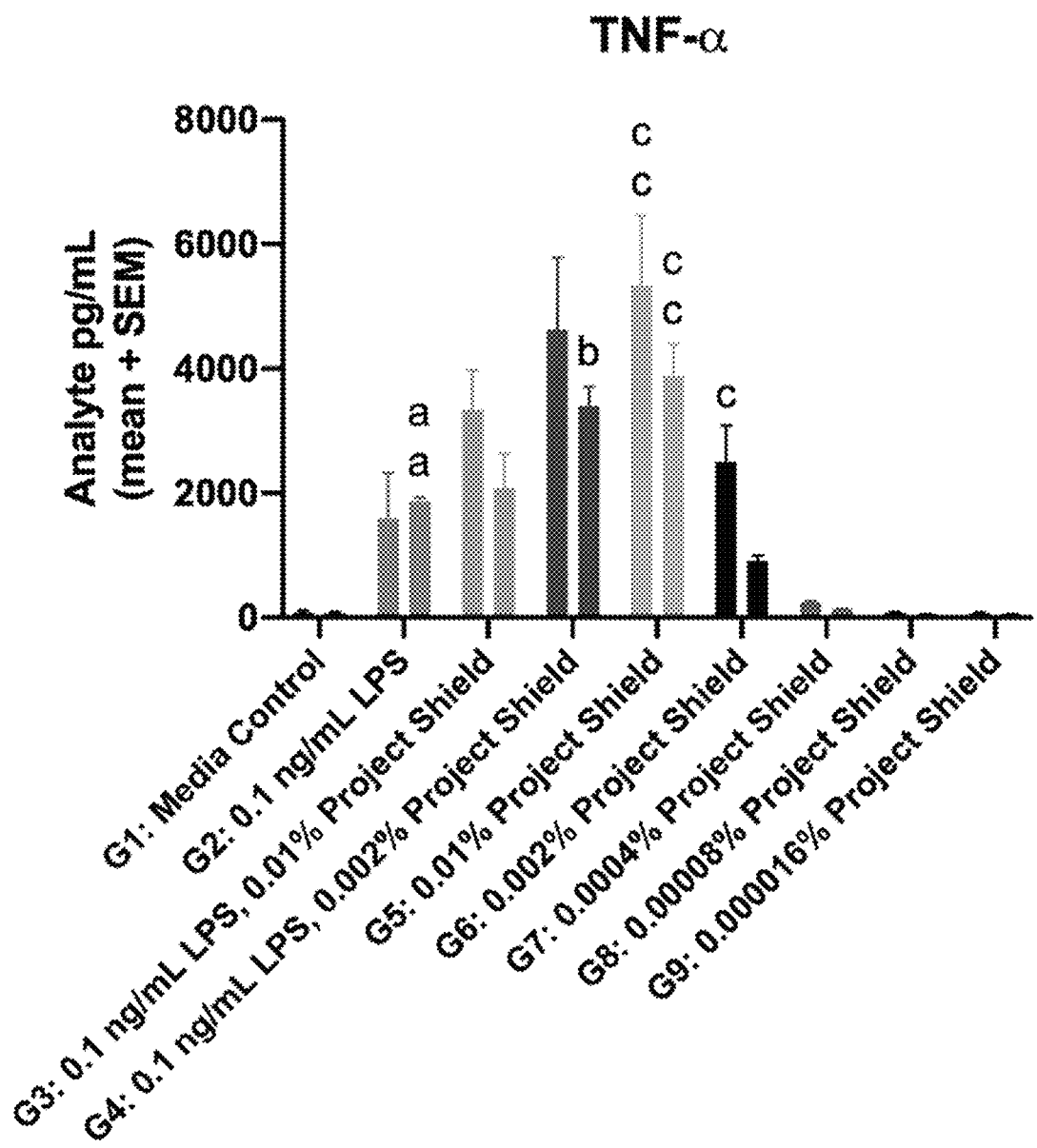
Figure 9:
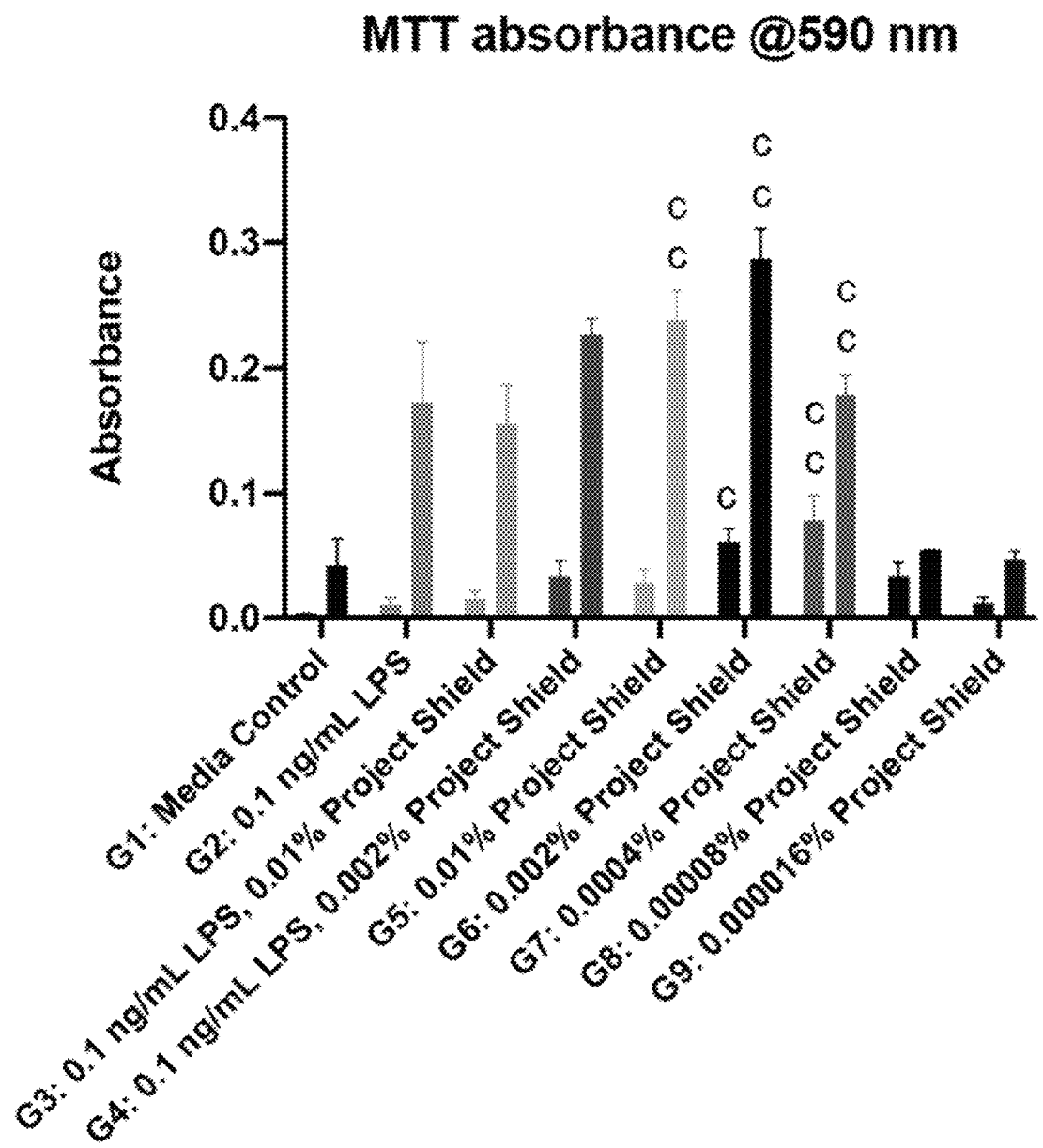

FIG. 8 is a bar graph illustrating exemplary results of increase in TNF-α activity at various concentrations of a natural-based composition, in accordance with various embodiments; and FIG. 9 is a bar graph illustrating exemplary results of cell proliferation measured using an MTT assay with an end point absorbance at 590 at various concentrations of a natural-based composition, in accordance with various embodiments, The drawings described herein are for illustrative purposes only of selected embodiments and not all possible implementations and are not intended to limit the scope of any of the exemplary embodiments disclosed herein or any equivalents thereof. It is understood that the drawings are not drawn to scale.

DESCRIPTION

The following disclosure is merely exemplary in nature and is in no way intended to limit the described embodiments, their application, or uses. The present invention has been described with reference to various exemplary embodiments.

Humans are interested in ways to support their immune system with natural ingredients with the hope of preventing of seasonal illness, or if sick, to boost their innate immunity to improve recovery time. In response, unique combinations of natural ingredients are described and enabled herein, which can support general innate immune function.

In some embodiments, a novel combination of natural ingredients comprises cyanidin-3-glucoside, andrographide, and a blend of antioxidants. The cyanidin-3-glucoside from black rice (*Oryza sativa*) can prevent the entry of viruses/viral infections into the cell. The andrographide can inhibit replication of viruses inside the cell. The antioxidant blend can increase the body's resilience (reduced oxidative stress) in response to infection.

An andrographis (*Andrographis paniculata*) extract can be a source of the andrographolides. A black rice (*Oryza sativa*) extract can be a source of the cyanidin-3-glucosides. The antioxidant blend can comprise an extract of at least one of: coffee, green tea, blackcurrant, blueberry, onion, apple, and acerola; and a concentrate of at least one of: camu camu, quercetin, tomato, broccoli, acai, turmeric, garlic, basil, oregano, cinnamon, elderberry, carrot, mangosteen, sweet cherry, blackberry, chokeberry, raspberry, spinach, kale, bilberry, brussel sprouts, and broccoli sprout.

In some embodiments, a novel combination of natural ingredients comprises cyanidin-3-glucoside, andrographide, a blend of antioxidants, prebiotic polysaccharides and beta-glucans. The prebiotic polysaccharides and beta-glucans can be extracted from mushrooms. More specifically, a Royal Agaricus Mushroom (*Agaricus blazei Murill*) extract can be a source of the beta-glucans, and a Turkey Tail Mushroom (*Coriolus versicolor*) extract can be a source of the polysaccharides.

Black or purple rice are cultivars of the species *Oryza sativa*. Rice is staple crop the world over and is not considered toxic in any capacity other than its potential to accumulate heavy metals from contaminated soil. The main difference between black rice and more common white and brown cultivars is the anthocyanin content that gives it the distinct purple/black appearance. The principle anthocyanin in black rice is cyanidin-3-glucoside, also called chrysanthemin, but other minor contributors have also been observed that include peonidin-3-glucoside and malvidin, depending on the cultivar.

The anthocyanin content, predominately cyanidin-3-glucoside, is also the principle anthocyanin of other known immune stimulating activity in humans. An anthocyanin extract from black rice provides the same immune boosting anthocyanins. An anthocyanin extract from black rice provides antioxidant support to help terminate free-radicals.

Phytochemical profiles of black rice are characterized by the presence of anthocyanins, which are a group of reddish to purple flavonoids that exist in black rice and other pigmented cereal grains. The main anthocyanins in black rice were found to be present in quantities more than 95% and were cyanidin 3-O-glucoside (2.8 mg/g) and peonidin-3-O-glucoside (0.5 mg/g) followed by flavones and flavonols (0.5 mg/g) and flavan-3-ols (0.3 mg/g). In addition, the identified flavones and flavonols were taxifolin, quercetin, apigenin, and luteolin. The concentrations of total anthocyanins in black rice cultivars significantly varied from one report to another, while higher concentrations of anthocyanins were detected in Chinese black-purple rice that contained cyanidin 3-O-glucoside (6.3 mg/g) and peonidin 3-O-glucoside (3.6 mg/g). The variations of the anthocyanin content in the reports on black rice might be due to the use of different cultivars and the variety of differing growing conditions.

Reports from HPLC-MS analysis state that four (4) anthocynidins have been found in black rice. The weight of each of anthocynidin as a percentage of the total weight of all anthocynidins weight is as follows: cyanidin-3-glucoside 91.01%, peonidin-3-glucoside 7.13%, cyanidin-3,5-diglucoside 0.92%, cyanidin-3-rutinoside 0.94%. The variations of the anthocyanin content in the reports on black rice might be due to the use of different cultivars and the variety of differing growing conditions.

In some embodiments, an anthocyanin-rich black rice extract significantly inhibits lipopolysaccharides ("LPS") that induced many pro-inflammatory mediators in RAW 264.7 macrophage white blood cells. The anthocyanin-rich black rice extract can increase the activity of TNF-α, and IL-6, which can effectively reduce the expression of two important inflammatory enzymes, the inducible NO synthase (iNOS) and the inducible cyclooxygenase-2 (COX-2). This results in an inhibition of the mitogen-activated protein kinase signaling pathway (MAPK pathway), leading to a decreased nuclear translocation of NF-κB and AP-1, two major transcription factors involved in the inflammation process.

In some embodiments, an anthocyanin-rich black rice extract has an anti-viral effect on cells that is mediated by interference in the hemagglutinin protein docking of the virus which is the means a virus enters the cell. Anthocyanin rich extracts are natural anti-virals. According to research results, an amount of anthocyanidin, specifically cyanidin-3-glucoside as the principle component, is sufficient to incur anti-viral effects against the infection cycle of influenza viruses. In addition, the anthocyanin-rich black rice extract can boost immunity in vivo.

In some embodiments, an anthocyanin-rich black rice extract significantly stimulates production of inflammatory cytokines IL-β, IL-6, IL-8 and TNF-α in monocytes. The anthocyanin-rich black rice extract can have potent immune stimulating activity in a dose-dependent manner on human peripheral monocytes.

In some embodiments, an anthocyanin-rich black rice extract can be an effective supplement for reducing symptoms associated with common upper respiratory tract infections.

Aerial parts of the plant *Andrographis paniculata* have been used for centuries in Chinese, Unani, and Ayurvedic medicine traditions. The plant itself is a rich source of bioactive phytonutrients including lactones, diterpenoids, flavonoids, and their glycosides. Uses range from antimicrobial, choleretic, hepatoprotective, adaptogenic effects, and the prevention and accelerated resolution of uncomplicated upper respiratory tract infections. The main actives are thought to be the lactones and diterpene compounds present in the leaves that include the compounds andrographolide, dehydroandrographolide, and bis-andrographolides A, B, C, and D.

In some embodiments, an andrographolide-rich *Andrographis* extract can have anti-viral effects in via post-entry mechanism that inhibits their replication abilities inside the cell. This is in contrast to the anti-viral effects of anthocyanidins, which appear to interfere with cell docking and cell entry. According to research results, an andrographolide-rich *Andrographis* extract has antibacterial effects that it exerts through anti-virulence and anti-inflammatory mechanisms.

In some embodiments, an andrographolide-rich *Andrographis* extract can enhance immunity through stimulation of hBD-2, a transient defensive molecule expressed in most epithelial cells when stimulated by pathogen invasion and that this is mediated through p38 MAPK pathways.

Vitamin C is an essential dietary micronutrient and is a required co-factor for numerous enzymes. It is a water-soluble vitamin that commonly exist in the body in its reduced form, ascorbic acid. Vitamin C functions as a reversible reductant antioxidant in aqueous fluid and tissues; the ability of it to donate electrons and be readily converted back to its reduced state by glutathione makes it a particularly potent antioxidant, and one that can replenish other antioxidants.

Almond mushroom (*Agaricus blazei*) is a mushroom that has been used for medicinal purposes. The main actives in an *Agaricus blazei* extract are the polysaccharides of (1→3), (1→6)-β-glucans, along with (1,4)-Galp and (1,4)-GalAp chains with terminal fucose residues, which act as immune adjuvants and demonstrate enhanced immune response in both in vitro and in vivo models of immune function. These polysaccrides stimulate the activity of T cells, B cells, NK cells, as well as others and can promote expression of interleukins, interferons, and other inflammatory modulators.

Turkey tail mushrooms (*Coriolus versicolor*) are some of the most common mushrooms around the world and are found near decomposing hardwood trees. Turkey tail mushrooms used extensively in traditional Chinese medicine. The some bioactive fractions of *Coriolus versicolor* are the water-soluble protein bound polysaccharides which are about 100 kDa in size. These bioactives can illicit anti-tumor, immune proliferation, and natural killer cell activation. Survey of literature supports historic traditional use of *Coriolus versicolor* as an immune booster and its clinical use as an immune adjuvant. The main immunostimulatory effect of a polysaccharides-rich *Coriolus versicolor* extract is mediated via its action on natural killer cells. In some embodiments, a polysaccharides-rich *Coriolus versicolor* extract enhances activation of leukocyte and neutrophil in an immunosuppressed condition in cell populations relevant to responding to the patients' disease.

An antioxidant blend can comprise an extract of at least one of: coffee, green tea, blackcurrant, blueberry, onion, apple, and acerola; and a concentrate of at least one of: camu camu, quercetin, tomato, broccoli, acai, turmeric, garlic, basil, oregano, cinnamon, elderberry, carrot, mangosteen, sweet cherry, blackberry, chokeberry, raspberry, spinach, kale, bilberry, brussel sprouts, and broccoli sprout. In some embodiments, the antioxidant blend can terminate free-radicals. In some embodiments, the antioxidant blend can provide significant reduction in circulating ROS levels which is a contributing part of the pathology associated with body's response to pathological infection. In some embodiments, the antioxidant blend can reduce cellular inflammatory response.

Interferon gamma ("IFNγ") is a cytokine that is critical for innate and adaptive immunity against viral, some bacterial and protozoal infections. More specifically, IFNγ is a lymphokine produced by immuno-active T lymphocytes and natural killer cells. It is important for host defense function, regulating cellular proliferation, differentiation, and apoptosis of lymphocytes. IFNγ is an important activator of macrophages and inducer of Class II major histocompatibility complex (MHC) molecule expression. Aberrant IFNγ expression is associated with a number of autoinflammatory and autoimmune diseases. The importance of IFNγ in the immune system stems in part from its ability to inhibit viral replication directly, and from its immunostimulatory and immunomodulatory effects. IFNγ is produced predominantly by natural killer (NK) and natural killer T (NKT) cells as part of the innate immune response, and by CD4 Th1 and CD8 cytotoxic T lymphocyte (CTL) effector T cells once antigen-specific immunity develops as part of the adaptive immune response.

Interleukin 1 beta ("IL-1β") is involved in modulation of autoimmune inflammation. IL-1β is a strong pro-inflammatory cytokine produced most prominently by cells associated with innate immunity, specifically monocytes and macrophages. It is induced in response to molecular signals associated with pathogens and dead host cells.

Interleukin 6 ("IL-6") stimulates the inflammatory and auto-immune processes. More specifically, IL-6 is an acute response inflammatory immune mediator involved in the detection of tissue damage, platelet production, stimulation of antibody production in B cells, as well as T cell differentiation. IL-6 is secreted by macrophages in response to specific microbial molecules, referred to as pathogen-associated molecular patterns (PAMPs). These PAMPs bind to an important group of detection molecules of the innate immune system, called pattern recognition receptors (PRRs), including Toll-like receptors (TLRs). These are present on the cell surface and intracellular compartments and induce intracellular signaling cascades that give rise to inflammatory cytokine production. IL-6 is an important mediator of fever and of the acute phase response. IL-6 is responsible for stimulating acute phase protein synthesis, as well as the production of neutrophils in the bone marrow. It supports the growth of B cells and is antagonistic to regulatory T cells.

Interleukin 8 ("IL-8") plays a role in the pathogenesis of bronchiolitis and other respiratory tract disease caused by viral infection. IL-8 can be secreted by any cells with TLRs that are involved in the innate immune response and has been demonstrated to be a signatory chemokine of CR2+ naive T cells also known as recent thymic emigrants. Typically, it is the macrophages that see an antigen first, and thus are the first cells to release IL-8 to recruit other cells. Both monomer and homodimer forms of IL-8 have been reported to be potent inducers of the chemokine receptors CXCR1 and CXCR2. The homodimer is more potent, but methylation of Leu25 can block the activity of homodimers. IL-8 is a member of the CXC chemokine family. IL-8 is secreted and is an important mediator of the immune reaction in the innate immune system response. The activity of IL-8 has distinct target specificity for increasing neutrophil and white blood cells.

Interleukin 10 ("IL-10") is a cytokine with multiple, pleiotropic, effects in immunoregulation and inflammation. IL-10 is an anti-inflammatory cytokine. It is important for immune modulation by limiting the immune response to pathogens to limit damage to the host. More specifically, IL-10 downregulates the expression of Th1 cytokines, MHC class II antigens, and co-stimulatory molecules on macrophages. It also enhances B cell survival, proliferation, and antibody production. IL-10 can block NF-κB activity and is involved in the regulation of the JAK-STAT signaling pathway. The function of IL-10 is an essential immunoregulator in the intestinal tract. Patients with Crohn's disease react favorably towards treatment with recombinant interleukin-10-producing bacteria, demonstrating the importance of IL-10 for counteracting the hyperactive immune response in the human body.

IL-12p40 and IL-12p70 are subunits of Interleukin 12 ("IL-12"). IL-12 also has anti-angiogenic activity, which means it can block the formation of new blood vessels. It does this by increasing production of interferon gamma, which in turn increases the production of a chemokine called inducible protein-10 (IP-10 or CXCL10). IP-10 then mediates this anti-angiogenic effect. Accordingly, IL-12 can induce immune response.

IL-12p40 (Interleukin-12, p40 subunit) is a necessary subcomponent of the active interleukin-12. By itself it is inert, but its formation as a homodimer serves as an antagonist to the natural IL-12 receptor and helps modulate IL-12 signaling.

IL-12p70 (Interleukin-12, p70 subunit) is the active IL-12 cytokine, which is a heterodimer of IL-12p40 and IL-12p35 subunits. IL-12 is produced by monocytes, macrophages, dendritic cells, and B cells to stimulate the activation of natural killer cells and T cells.

Tumor Necrosis Factor alpha ("TNF-α") is a cytokine used by the immune system for cell signaling. If macrophages detect an infection, they release TNF in order to alert other cells of the immune system as well as cells of other tissues, leading to inflammation. The primary role of TNF is in the regulation of immune cells. More specifically, TNF-α is an inflammatory cytokine produced by white blood cells (macrophages and monocytes) during acute inflammation. It is responsible for numerous signaling cascades within cells that can lead to necrosis or apoptosis; it is an important chemical mediator for resistance to infection.

In some embodiments, a dosage of the composition comprises 90 mg of Vitamin C, 500 mg of Royal Agaricus Mushroom (*Agaricus blazei Murill*) extract containing beta-glucan; 400 mg of Turkey Tail Mushroom (*Coriolus versicolor*) extract containing polysaccharides; 100 mg of an Antioxidant Blend; 60 mg of Andrographis (*Andrographis paniculata*) extract containing andrographolides, and 50 mg of Black Rice (*Oryza sativa*) extract containing cyanidin-3-glucosides.

Anthocyanin toxicity has not been demonstrated in humans to date, nor have any animal toxicology studies identified toxicity associated with anthocyanin intake. A joint FAO/WHO expert Committee on Food Additives suggests an acceptable daily intake of 2.5 mg/kg per day for anthocyanins. Anthocyanin rich extracts, reviewed by the EFSA determined potential safety concerns were unlikely.

Example 1

An exemplary natural-based composition is evaluated in an in vitro Peripheral Blood Monocyte Cells cellular inflammation model.

The exemplary composition (named "Project Shield") comprises 7.5 wt % of Vitamin C, 41.6 wt % of Royal Agaricus Mushroom (*Agaricus blazei Murill*) extract containing beta-glucan; 33.3 wt % of Turkey Tail Mushroom (*Coriolus versicolor*) extract containing polysaccharides; 8.3 wt % of Antioxidant Blend; 5 wt % of Andrographis (*Andrographis paniculata*) extract containing andrographolides, and 4.16 wt % of Black Rice (*Oryza sativa*) extract containing cyanidin-3-glucosides, (wt % is weight percent of total weight of exemplary composition).

Test Method

Test Item Preparation: 120 mg of the exemplary composition (Project Shield) was dissolved in 6000 μL of CGM on the day of use to create a 2% (w/v) Dilution Stock Solution. A 2 ng/mL Working Stock of Lipopolysaccharides ("LPS") was prepared fresh with IM and stored at 2-8° C. 10 μL LPS (2 ng/mL) was added to the appropriate wells for a final concentration of 0.1 ng/mL.

Complete Growth Media (CGM): To formulate CGM, RPMI was supplemented with 10% FBS and 100 U/mL penicillin+100 μg/mL streptomycin. CGM was prepared aseptically and stored at 2-8° C. for the duration of the study. CGM was warmed to 37° C. prior to use.

Cell Culture Set-up: Cells were thawed according to manufacturer's instructions, washed in CGM and assessed for viability using trypan blue staining. A stock cell solution of $2\times10^6$ cells/mL suspended in CGM was prepared. 100 μL of the stock solution was added to appropriate wells of a 96-well plate to seed $2\times10^5$ cells per well. Cells were incubated at 37° C. with 5% $CO_2$ for one hour.

Test System: Cryopreserved Human Peripheral Blood Monocyte Cells (PBMCs) in RPMI 1640+10% heat inactivated FBS+100 U/mL penicillin+100 ug/mL streptomycin (complete growth medium: CGM).

TABLE 2

Test Groups

| Group No. | Stimulant | Treatment |
| --- | --- | --- |
| 1 | Media Control | N/A |
| 2 | LPS (0.1 ng/mL) | Media |
| 3 | LPS (0.1 ng/mL) | Project Shield 0.01% (w/v) |
| 4 | LPS (0.1 ng/mL) | Project Shield 0.002% (w/v) |
| 5 | Project Shield 0.01% (w/v) | N/A |
| 6 | Project Shield 0.002% (w/v) | N/A |
| 7 | Project Shield 0.0004% (w/v) | N/A |
| 8 | Project Shield 0.00008% (w/v) | N/A |
| 9 | Project Shield 0.000016% (w/v) | N/A |

Test Method: A: Cryopreserved PBMCs Seeded; B: Treatments/Stimulants Addition; C: Collection of 24-hour supernatants (40 μL off top); D: Harvest 48-hour cell culture supernatants for cytokine analysis and perform MTT assay MTT Assay: The cells pelleted by centrifugation at 48 hours were used to perform an MTT assay. Briefly, cells were resuspended in 50 μL of serum-free media and 50 μL of MTT solution for each well. The plate was incubated at 37° C. for 3 hours. After incubation, 150 μL of MTT solvent was added to each well. The plate was wrapped in foil and shaken on an orbital shaker for 15 minutes. The absorbance was read at 590 nm.

Test Results: Cell proliferation was measured using an MTT assay. The resulting end point absorbance at 590 nm is shown in FIG. 9. Two individual donors are shown (each having 3 averaged replicates) for each treatment group As illustrated in FIGS. 1-8, inflammatory cytokine expression for cell supernatants at 48 hours post stimulation/treatment. Expression was assessed by multiplex using the Luminex platform for the following cytokines: IFNγ, IL-1β, IL-6, IL-8, IL-10, IL-12p40, IL-12p70, TNF-α. Two individual donors are shown (each having 3 averaged replicates) for each treatment group.

Figure 1:
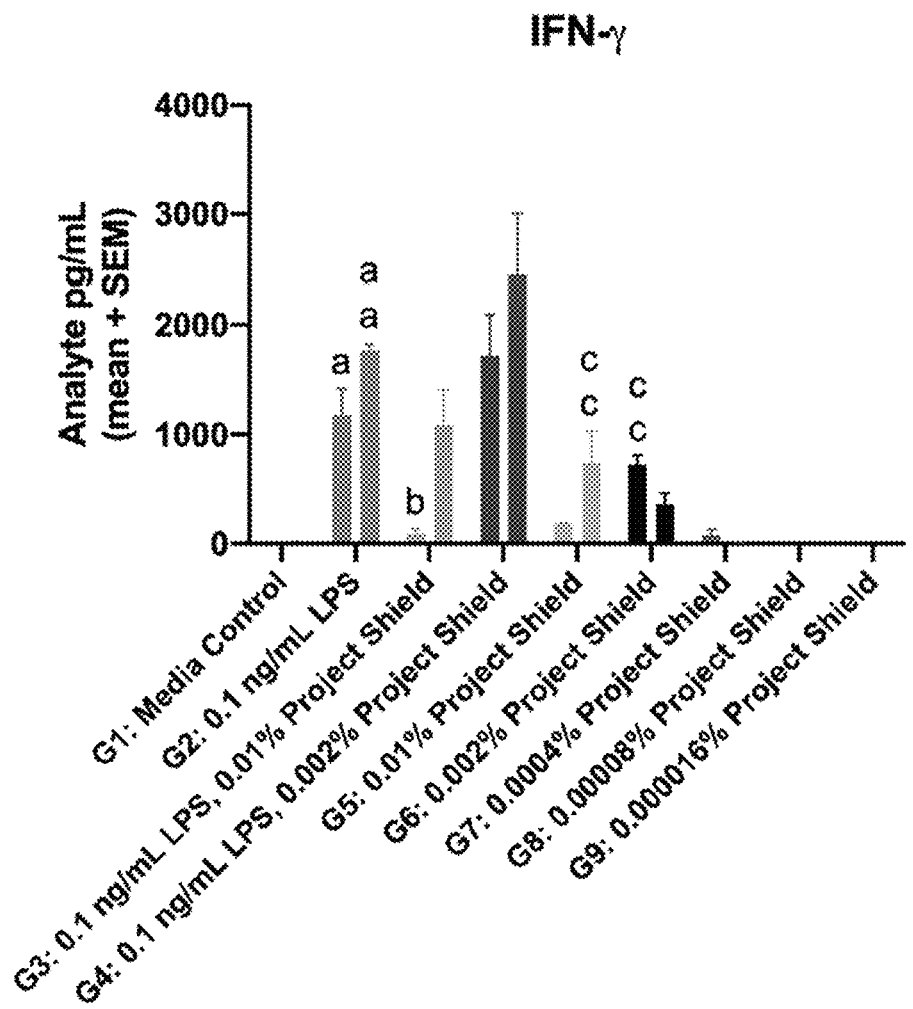
FIG. 1 is a bar graph illustrating exemplary results of increase in IFNγ activity at various concentrations of a natural-based composition, in accordance with various embodiments.

The bar graph in FIG. 1 illustrates a statistically significant increase in IFNγ activity at various concentrations of the exemplary composition named Project Shield as labeled on the x-axis. IFNγ for both donors 1 and 2 was significantly increased for the LPS control Group indicating the inflammation model is functioning as expected. Treatment with 0.01% Project shield resulted in significant inhibition on IFNγ induced by LPS in Donor 1, but not in Donor 2. Project Shield alone at 0.002% in Donor 1 and 0.01% in Donor 2 showed a statistically significant increase in IFNγ levels relative to the Media Control.

Figure 2:
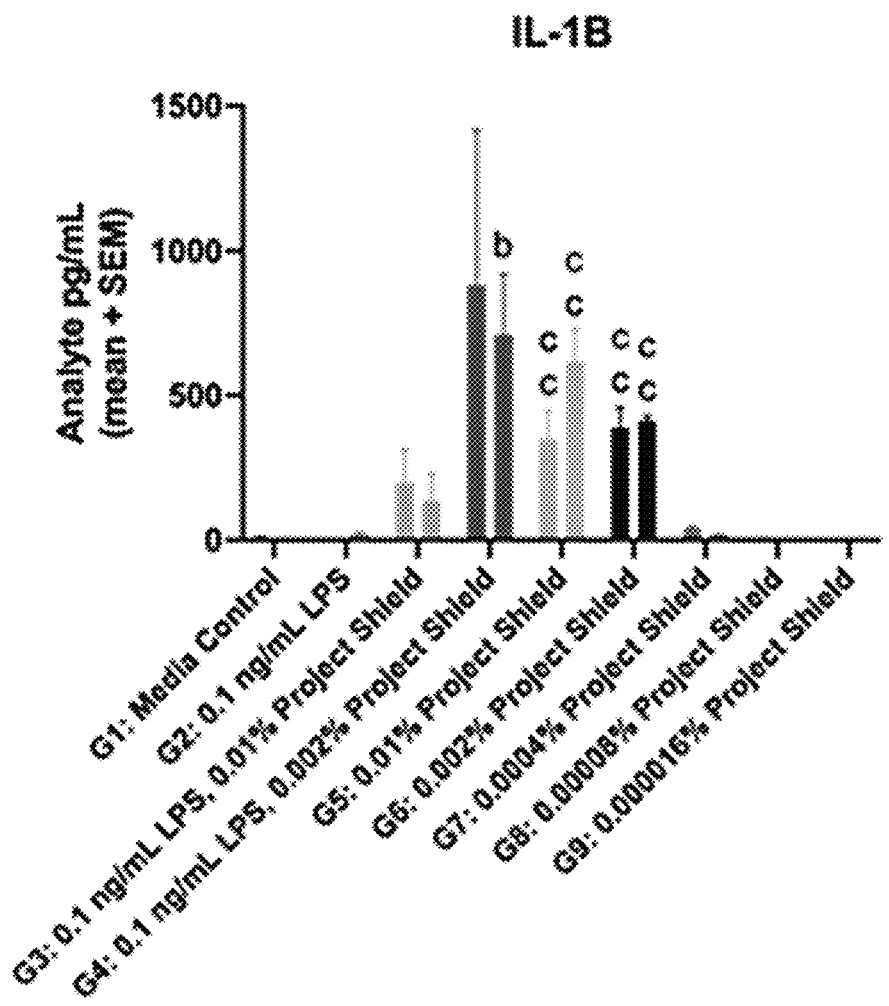
FIG. 2 is a bar graph illustrating exemplary results of increase in IL-1B activity at various concentrations of a natural-based composition, in accordance with various embodiments.

The bar graph in FIG. 2 illustrates a statistically significant increase in increase in IL-1γ activity at various concentrations of the exemplary composition named Project Shield as labeled on the x-axis. IL-1β for both donors 1 and 2 was not significantly increased for the LPS control Group. Treatment with 0.002% Project Shield combined with 0.1 ng/mL LPS resulted in a significant increase of IL-1β in Donor 2, but not in Donor 1 relative to just treatment with 0.1 ng/mL LPS. Project Shield alone at both 0.01% and 0.002% in Donor 1 and Donor 2 showed a statistically significant increase in IL-10 levels relative to the Media Control.

Figure 3:
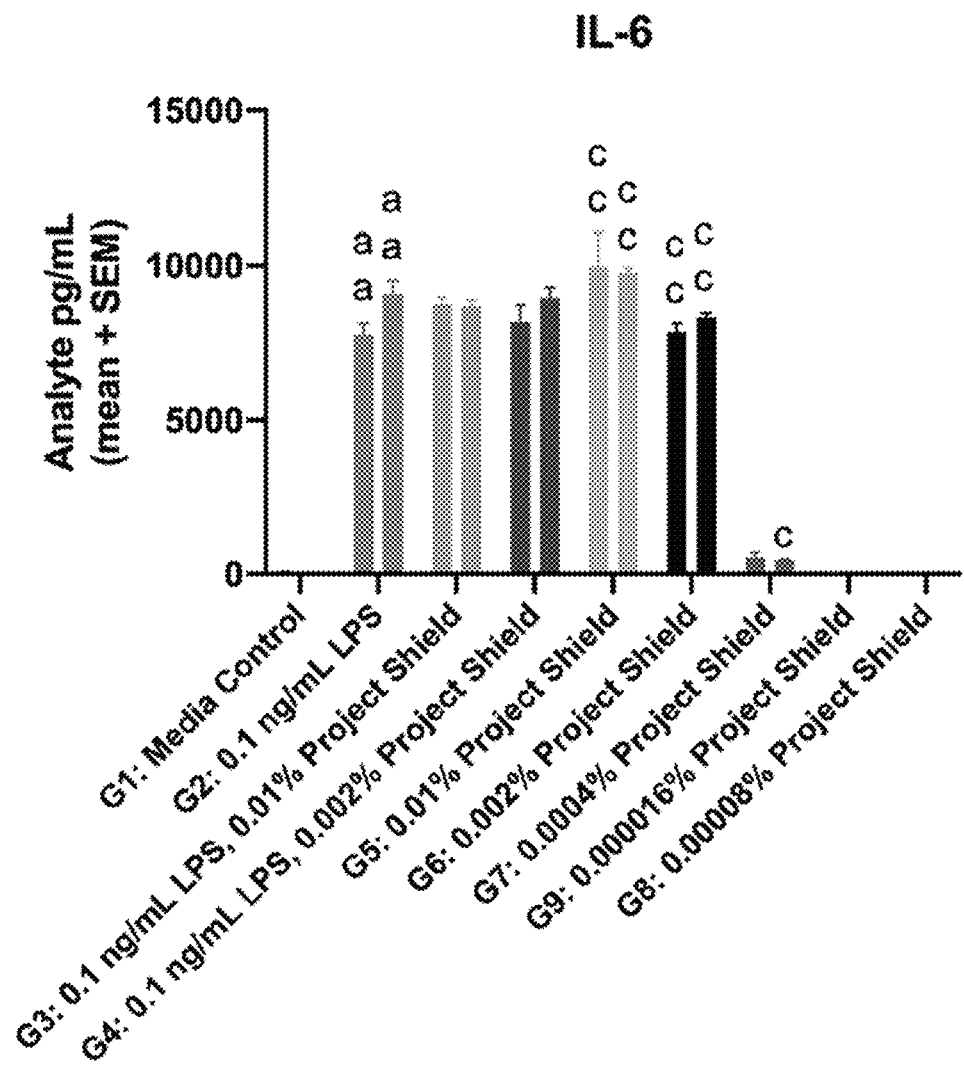
FIG. 3 is a bar graph illustrating exemplary results of increase in IL-6 activity at various concentrations of a natural-based composition, in accordance with various embodiments.

The bar graph in FIG. 3 illustrates a statistically significant increase in increase in IL-6 activity at various concentrations of the exemplary composition named Project Shield as labeled on the x-axis. IL-6 for both donors 1 and 2 was significantly increased for the LPS control Group indicating the inflammation model is functioning as expected. Treatment with Project Shield combined with 0.1 ng/mL LPS did not significantly impact IL-6 levels for Donor 1 or Donor 2 relative to just treatment with 0.1 ng/mL LPS. Project shield alone at 0.01%, 0.002%, and 0.0004% in Donor 1 showed a statistically significant increase in IL-6 levels relative to the Media Control. Project Shield alone at 0.01% and 0.002% in Donor 2 showed a statistically significant increase in IL-6 levels relative to the Media Control.

Figure 4:
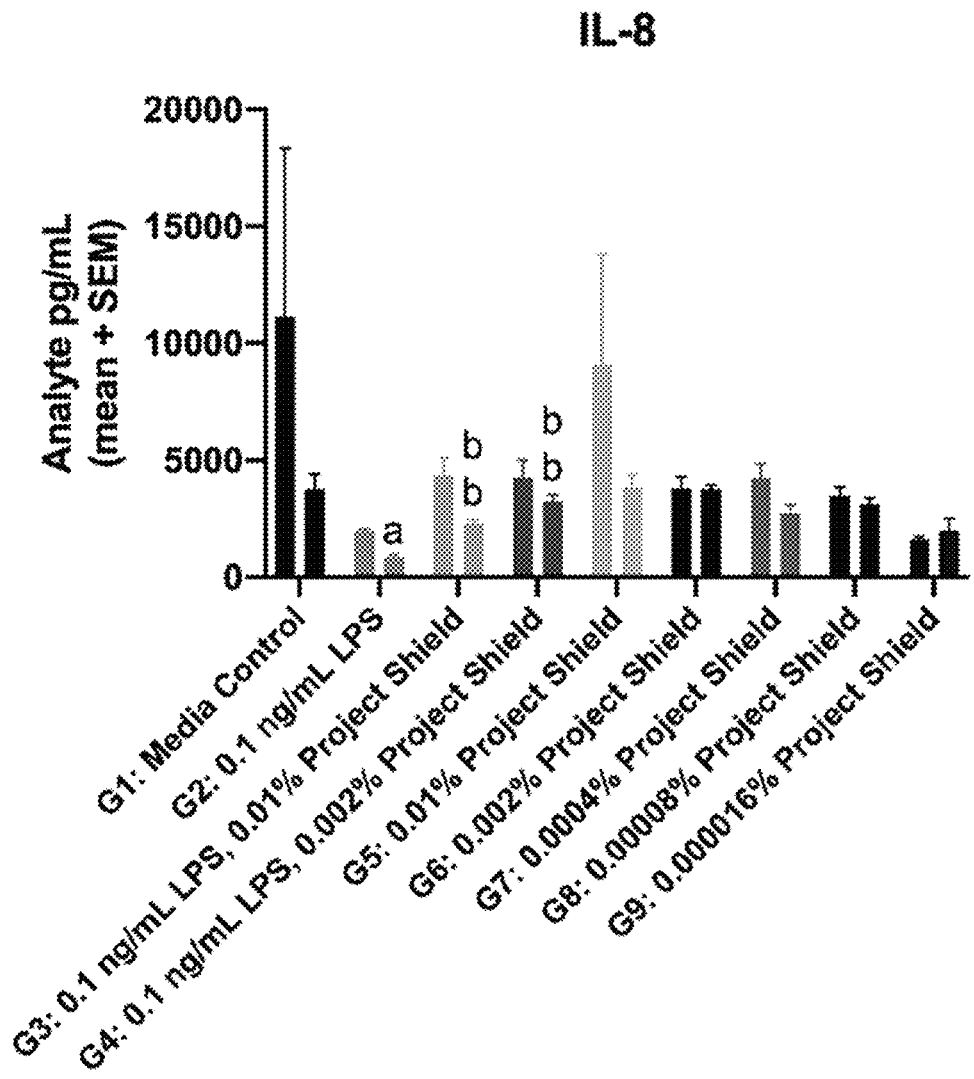
FIG. 4 is a bar graph illustrating exemplary results of increase in IL-8 activity at various concentrations of a natural-based composition, in accordance with various embodiments.

The bar graph in FIG. 4 illustrates a statistically significant increase in increase in IL-8 activity at various concentrations of the exemplary composition named Project Shield as labeled on the x-axis. IL-8 for donor 2, but not donor 1 was significantly increased for the LPS control Group. Treatment with 0.01% and 0.002% Project Shield combined with 0.1 ng/mL LPS resulted in a significant increase in IL-8 for donor 2, but not donor 1 relative to just treatment with 0.1 ng/mL LPS. Project Shield alone did not show any significant difference relative to the Media Control.

Figure 5:
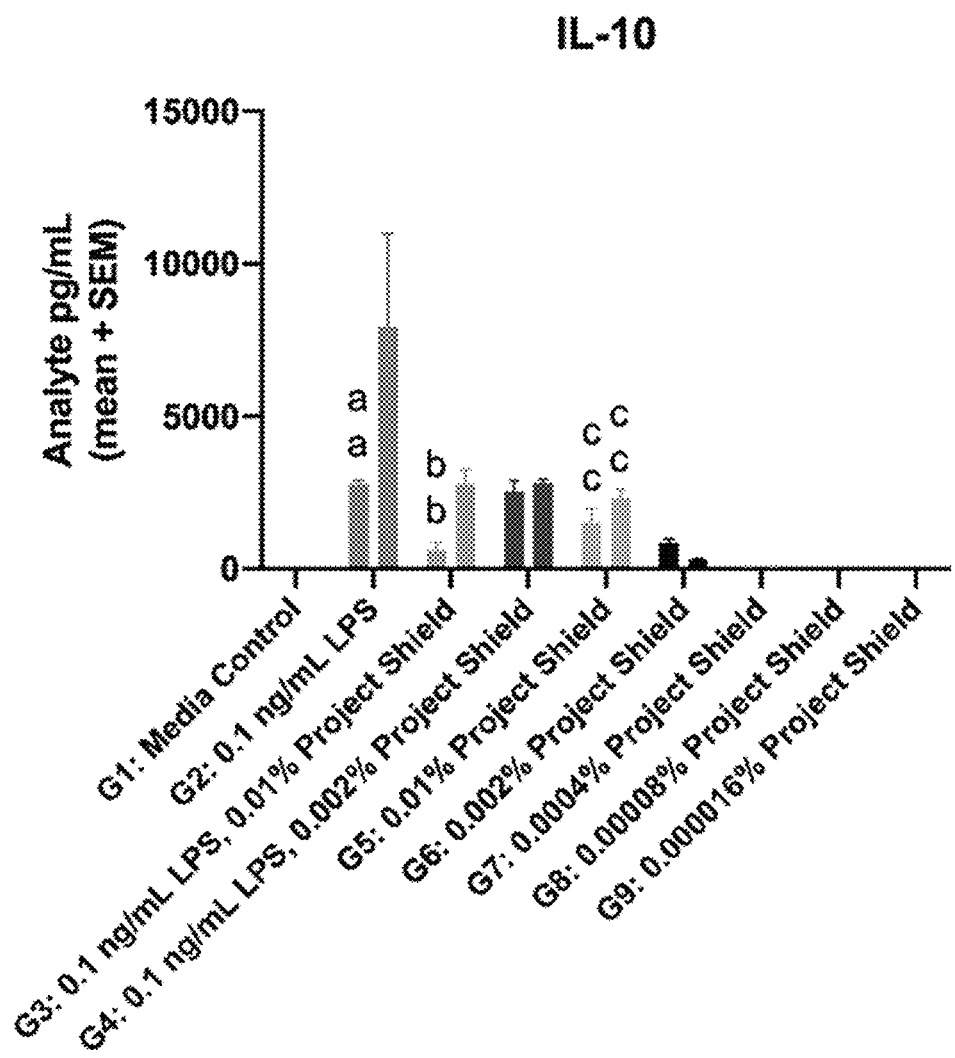
FIG. 5 is a bar graph illustrating exemplary results of increase in IL-10 activity at various concentrations of a natural-based composition, in accordance with various embodiments.

The bar graph in FIG. 5 illustrates a statistically significant increase in increase in IL-10 activity at various concentrations of the exemplary composition named Project Shield as labeled on the x-axis. IL-10 for donor 1, but not donor 2 was significantly increased for the LPS control Group. Treatment with 0.01% Project Shield resulted in significant inhibition on IL-10 induced by LPS in Donor 1, but not in Donor 2. Project Shield alone at 0.01% in Donor 1 and Donor 2 showed a statistically significant increase in IL-10 levels relative to the Media Control.

Figure 6:
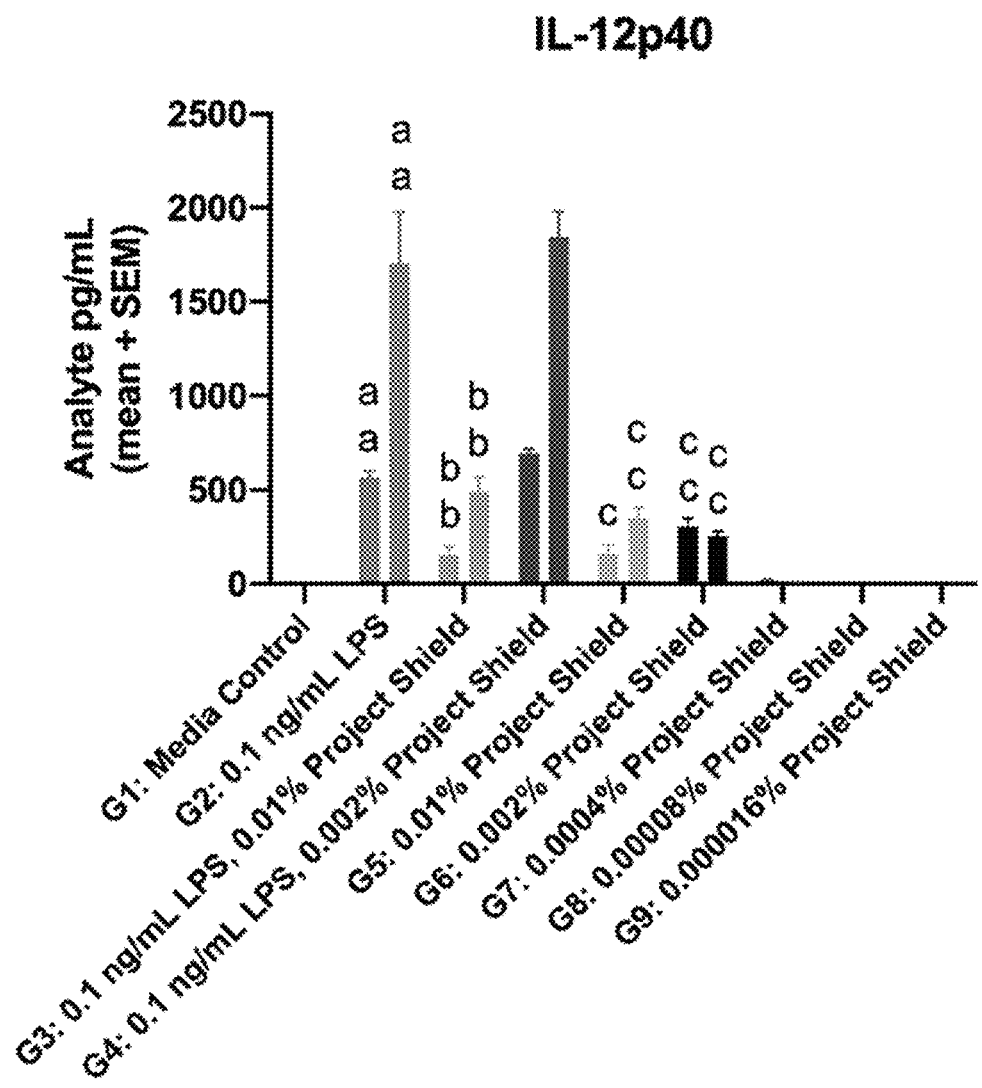
FIG. 6 is a bar graph illustrating exemplary results of increase in IL-12p40 activity at various concentrations of a natural-based composition, in accordance with various embodiments.

The bar graph in FIG. 6 illustrates a statistically significant increase in increase in IL-12p40 activity at various concentrations of the exemplary composition named Project Shield as labeled on the x-axis. IL-12p40 for both donors 1 and 2 was significantly increased for the LPS control Group indicating the inflammation model is functioning as expected. Treatment with 0.01% Project Shield resulted in significant inhibition on IL-12p40 induced by LPS in Donor 1 and Donor 2. Project Shield alone at 0.01% and 0.002% in Donor 1 and Donor 2 showed a statistically significant increase in IL-12p40 levels relative to the Media Control.

Figure 7:
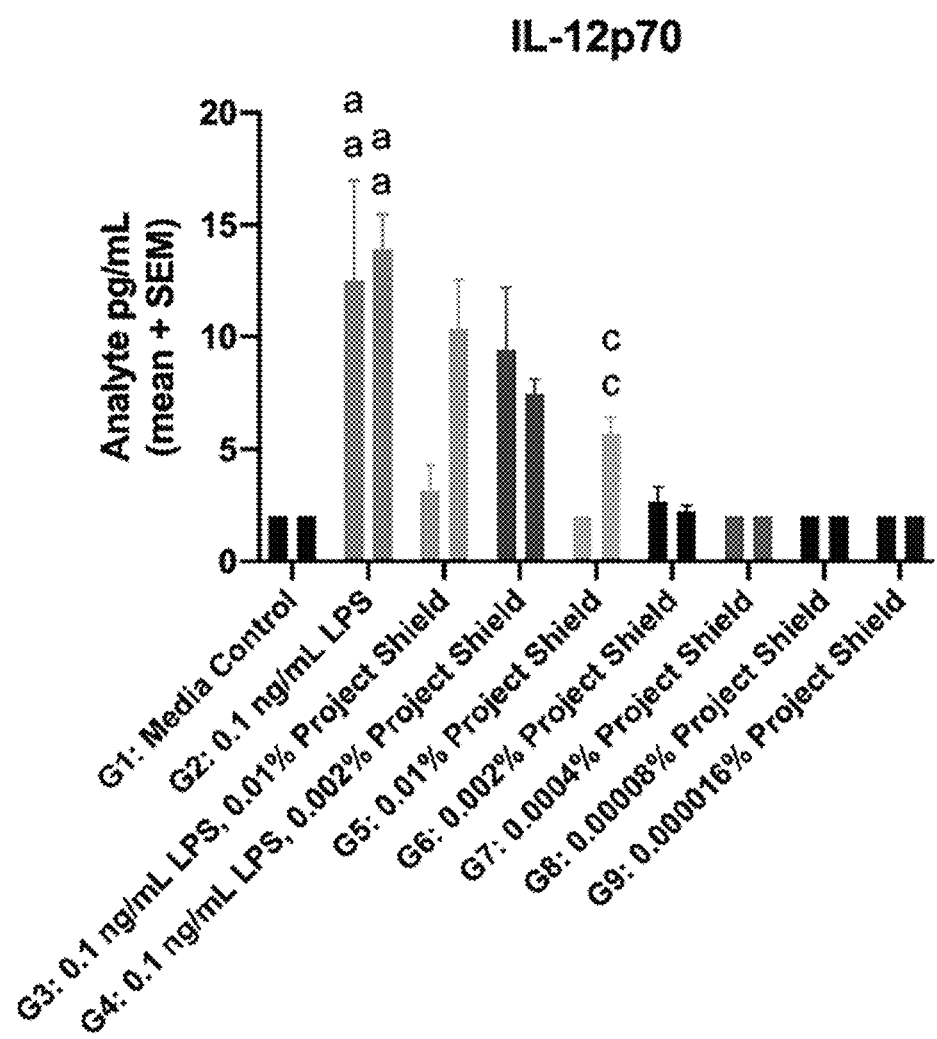
FIG. 7 is a bar graph illustrating exemplary results of increase in IL-12p79 activity at various concentrations of a natural-based composition, in accordance with various embodiments.

The bar graph in FIG. 7 illustrates a statistically significant increase in increase in IL-12p70 activity at various concentrations of the exemplary composition named Project Shield as labeled on the x-axis. IL-12p70 for both donors 1 and 2 was significantly increased for the LPS control Group indicating the inflammation model is functioning as expected. Treatment with Project Shield combined with 0.1 ng/mL LPS did not exhibit any statistical difference relative to the LPS control Group. Project Shield alone at 0.01% in Donor 2, but not Donor 1 showed a statistically significant increase in IL-12p70 levels relative to the Media Control.

The bar graph in FIG. 8 illustrates a statistically significant increase in increase in TNF-α activity at various concentrations of the exemplary composition named Project Shield as labeled on the x-axis. TNF-α for donor 2, but not donor 1 was significantly increased for the LPS control Group. Treatment with 0.002% Project shield combined with 0.1 ng/mL LPS resulted in a significant increase of TNF-α in Donor 2, but not in Donor 1 relative to just treatment with 0.1 ng/mL LPS. Project shield alone at 0.001% and 0.002% in Donor 1 and 0.01% in Donor 2 showed a statistically significant increase in TNF-α levels relative to the Media Control.

The bar graph in FIG. 9 illustrates exemplary results of cell proliferation measured using a MTT assay with an end point absorbance at 590 at various concentrations of the composition named Project Shield. Project Shield caused a statistically significant increase in PBMC proliferation relative to the Media Control group as measured by an MTT Assay. This increase was statistically significant for Donor 1 at 0.002% and 0.0004% Project Shield as well as for Donor 2 at 0.01%, 0.002%, and 0.0004% Project Shield.

Example 2

The Test Method is the protocol as described above, however, the Test Group had higher concentrations of the same composition named Project Shield as defined in Table 3. Each experimental group listed in Table 3 has 3 donors and each of these 3 donors was plated in triplicate.

TABLE 3

| Group No. | Stimulant | Treatment |
| --- | --- | --- |
| 1 | Media Control | N/A |
| 2 | LPS (0.1 ng/mL) | Media |
| 3 | LPS (0.1 ng/mL) | Project Shield 5% (w/v) |
| 4 | LPS (0.1 ng/mL) | Project Shield 1% (w/v) |
| 5 | Project Shield 5% (w/v) | N/A |
| 6 | Project Shield 1% (w/v) | N/A |
| 7 | Project Shield 0.5% (w/v) | N/A |
| 8 | Project Shield 0.1% (w/v) | N/A |
| 9 | Project Shield 0.05% (w/v) | N/A |

While the control groups (LPS only or media control) behaved normally, most of the cytokine levels were below the detection limits with project shield treatments from 0.05 to 5%. The lowest concentration (0.05%) showed measurable cytokine concentration values for some cytokines while a higher concentration of project shield for the same cytokine did not. This result indicated that concentrations of Project Shield were too high for the cells and the PBMCs were unable to survive the current concentrations of Project Shield.

Observations during the study that could further indicate the possible cytotoxic effects from high concentration of Project Shield. Before seeding the PBMCs, cell viability was checked and found to be 99.14%, 94.40%, and 92.23% for donors 1, 2, and 3 respectfully. Cells were periodically visually checked at all stages of the study and found to be visually present (although this does not mean they are alive when checked). Cells not receiving project shield behaved normally in all tests compared to historical data.

For both Examples, statistical comparisons between treatment groups were performed independently for each donor.

A Student's unpaired T-test was performed on Groups 1 and 2, significant differences are indicated above columns for Group 1. Significance is indicated with "a" (p<0.05) and "aa" (p<0.01). An Ordinary one-way ANOVA was performed on Groups 2-4 followed by Dunnett's multiple comparisons of each group compared to the LPS only group (Group 2). Significant differences are indicated above the appropriate columns. Significance is indicated with "b" (p<0.05) and "bb" (p<0.01). An Ordinary one-way ANOVA was performed on Groups 1 and 5-9 followed by Dunnett's multiple comparisons of each group compared to the Media Control group (Group 1). Significant differences are indicated above the appropriate columns. Significance is indicated with "c" (p<0.05) and "cc" (p<0.01).

As illustrated by the results, administering the exemplary composition named Project Shield can increase immune response. In addition, the results validate that administering the exemplary composition named Project Shield can increase the activity of at least one of IFNγ, IL-1β, IL-6, IL-8, IL-10, IL-12p40, IL-12p70, TNF-α.

The results validate that administering the exemplary composition named Project Shield can modulate autoimmune inflammation. The results validate that administering the exemplary composition named Project Shield can prevent bronchiolitis and other respiratory tract disease caused by viral infection.

The above Examples demonstrate that (1) Project shield can significantly increase the cell viability/proliferation of PBMCs when given at the lower concentrations of 0.01%, 0.002%, and 0.0004%; and (2) Project Shield exhibits both stimulatory and inhibitory properties for the cytokines tested.

This Examples show (1) when PBMC's were treated with 0.1 ng/mL LPS, Project Shield showed inhibitory effects on IFN-γ, IL-10, and IL-12p40 depending on the specific concentration and donor; and (2) when PBMC's were treated with just Project Shield, stimulatory effects were observed for IFN-γ, IL-1B, IL-6, IL-10, IL-12p40, IL-12p70, and TNF-α depending on the specific concentration and donor.

Various embodiments provide an immune-enhancing natural-based composition, which has both stimulatory and inhibitory properties for the cytokines. In some embodiments, the cytokines consist of one or more of IFN-γ, IL-1B, IL-6, IL-10, IL-12p40, IL-12p70, and TNF-α. An example of the immune-enhancing natural-based composition is the composition named Project Shield, as studied in the Examples.

In some embodiments, the immune-enhancing natural-based composition increases immunity of a subject by increasing expression of one or more of IFN-γ, IL-1B, IL-6, IL-10, IL-12p40, IL-12p70, and TNF-α. In some embodiments, the immune-enhancing natural-based composition increases immunity of a subject by increasing expression of IFN-γ, IL-1B, IL-6, IL-10, IL-12p40, IL-12p70, and TNF-α.

In some embodiments, the immune-enhancing natural-based composition increases immunity of a subject by decreasing expression of one or more of IFN-γ, IL-1B, IL-6, IL-10, IL-12p40, IL-12p70, and TNF-α, when the subject is infected by a pathogen. In some embodiments, the immune-enhancing natural-based composition increases immunity of a subject by decreasing expression of IFN-γ, IL-1B, IL-6, IL-10, IL-12p40, IL-12p70, and TNF-α, when the subject is infected by a pathogen.

Various embodiments provide a method of increasing immunity in a subject. The method can comprise: administering to the subject one or more effective doses of an immune-enhancing natural-based composition, thereby stimulating increased expression of one or more of IFN-γ, IL-1B, IL-6, IL-10, IL-12p40, IL-12p70, and TNF-α. Of course, the subject can be a human, however, the subject can be a mammal.

In some embodiments of the method, the administering to the subject one or more effective doses of an immune-enhancing natural-based composition, thereby prevents the entry of viruses into the cell. In some embodiments of the method, the administering to the subject one or more effective doses of an immune-enhancing natural-based composition, thereby inhibits replication of viruses inside the cell. In some embodiments of the method, the administering to the subject one or more effective doses of an immune-enhancing natural-based composition, thereby reducing reduced oxidative stress in response to infection. The method can include increasing immunity to viral infections.

Various embodiments provide a method of increasing immunity to a virus in a subject. The method can comprise: administering to the subject one or more effective doses of an immune-enhancing natural-based composition, thereby increasing an anti-viral effect on cell of the subject mediated by interference in the hemagglutinin protein docking of the virus. In some embodiments, the anti-viral effects prevent the infection cycle of influenza viruses.

Various embodiments provide a method of increasing immunity to a virus in a subject. The method can comprise: administering to the subject one or more effective doses of an immune-enhancing natural-based composition, thereby stimulating increased expression one or more of IFN-γ, IL-1B, IL-6, IL-10, IL-12p40, IL-12p70, and TNF-α; inhibiting replication of the virus inside a cell of the subject, and preventing entry of virus into the cell.

Various embodiments provide a method of increasing immunity to a virus in a subject. The method can comprise: administering to the subject one or more effective doses of an immune-enhancing natural-based composition, thereby increasing an anti-viral effect on a cell of the subject mediated by interference in the hemagglutinin protein docking of the virus, stimulating increased expression of one or more of IFN-γ, IL-1B, IL-6, IL-10, IL-12p40, IL-12p70, and TNF-α, inhibiting replication of the viruses inside the cell, and reducing oxidative stress on the cell.

In some embodiments, methods increase immunity to viral upper respiratory tract infections. In some aspects, the viral upper respiratory tract infection can be from COVID-19. In some embodiments, methods increase immunity to COVID-19.

Various embodiments provide a method of increasing immunity to a pathogen in a subject can comprise: administering to the subject one or more effective doses of an immune-enhancing natural-based composition, thereby reducing oxidative stress and stimulating increased expression of IFN-γ, IL-1B, IL-6, IL-10, IL-12p40, IL-12p'70, and TNF-α.

Some of the methods are effective in increasing immunity to viral infections, such as COVID-19.

According to some of the methods, the immune-enhancing natural-based composition comprises 7.5 wt % of Vitamin C, 41.6 wt % of *Agaricus blazei Murill* extract containing beta-glucan; 33.3 wt % of *Coriolus versicolor* extract containing polysaccharides; 8.3 wt % of an antioxidant blend; 5 wt % of *Andrographis paniculata* extract containing andrographolides, and 4.16 wt % of *Oryza sativa* extract containing cyanidin-3-glucosides.

In some embodiments of the methods, the extract of *Oryza sativa* comprises at least 25% by weight of cyanidin-3-glucosides; the extract of *andrographis paniculata* comprises at least 50% by weight of andrographolides; the extract of *agaricus blazei* comprises at least 50% by weight of beta glucans; the extract of *coriolus versicolor* comprises at 50% by weight polysaccharides.

According to some of the methods, the immune-enhancing natural-based composition is a mixture of an extract of *Oryza sativa* comprising at least 25% by weight of cyanidin-3-glucosides; an extract of *andrographis paniculata* comprising at least 50% by weight of andrographolides; ascorbic acid; an extract of *agaricus blazei* comprising at least 50% by weight of beta glucans; an extract of *coriolus versicolor* comprising at 50% by weight polysaccharides; and at least one antioxidant.

According to some of the methods, the immune-enhancing natural-based composition comprises cyanidin-3-glucosides in a range from 2% to 6% by weight; andrographolides in a range from 3% to 7% by weight; ascorbic acid is in a range from 9% to 13% by weight; beta glucans is in a range from 38% to 42% by weight; polysaccharides is in a range from 30% to 34% by weight; and at least one antioxidant is in a range from 6% to 10% by weight.

According to some of the methods, the effective dose of an immune-enhancing natural-based composition comprises: 30-70 mgs of cyanidin-3-glucosides; 40-80 mgs of andrographolides; 75-125 mgs of ascorbic acid; 400-600 mgs of beta glucans; 300-500 mgs of polysaccharides; and 75-125 mgs of a blend of antioxidants.

Various embodiments provide a capsule comprising: 8-10 wt % of Vitamin C, 30-36 wt % of *Agaricus blazei Murill* extract containing beta-glucan; 25-28 wt % of *Coriolus versicolor* extract containing polysaccharides; 5-9 wt % of an antioxidant blend; 3-6 wt % of *Andrographis paniculata* extract containing andrographolides, 2-5 wt % of *Oryza sativa* extract containing cyanidin-3-glucosides, and 15-20% capsule and binders.

In some embodiments, an immune enhancing capsule consisting of: 6-7 wt % of Vitamin C, 33-34 wt % of *Agaricus blazei Murill* extract containing beta-glucan; 26-27 wt % of *Coriolus versicolor* extract containing polysaccharides; 6-7 wt % of antioxidants; 4-5 wt % of *Andrographis paniculata* extract containing andrographolides, 3-4 wt % of *Oryza sativa* extract containing cyanidin-3-glucosides, and 16-17% capsule and binders.

In some embodiments, an immune enhancing capsule consisting of: about 65 mg of Vitamin C, about 125 mg of beta-glucan; about 100 mg of polysaccharides; about 50 mg of antioxidants; about 15 mg of andrographolides, and about 6% of cyanidin-3-glucosides. In one embodiment, the capsule and binders weight about 120 mg. In another embodiment, the capsule and binders weight about 150 mg. the capsule and binders weight between 120 mg and 250 mg.

Various embodiments provide a composition in the form of tablets, wafer capsules, gel capsules, sticks, sachets, vials, droppers or in injectable form. The composition can contain a mixture of: an extract of black rice comprising at least 25% by weight of cyanidin-3-glucosides; an extract of *andrographis paniculata* comprising at least 50% by weight of andrographolides; ascorbic acid; an extract of *agaricus blazei* comprising at least 50% by weight of beta glucans; an extract of *coriolus versicolor* comprising at 50% by weight polysaccharides; and at least one antioxidant.

In some embodiments, a weight ratio of the cyanidin-3-glucosides to the andrographolides is in a range from 1:1 to 1:2.

The mixture can comprise: the cyanidin-3-glucosides is in a range from 2% to 6% by weight; the andrographolides is in a range from 3% to 7% by weight; the ascorbic acid is in a range from 9% to 13% by weight; the beta glucans is in a range from 38% to 42% by weight; the polysaccharides is in a range from 30% to 34% by weight; and the at least one antioxidant is in a range from 6% to 10% by weight.

Some embodiments provide a method of increasing immunity to viral infections in human and animal patients, the method comprising administering to the patient the composition containing the mixture.

Some of the methods are effective in increasing immunity to upper respiratory tract infections Some of the methods are effective in increasing immunity to viral infections, such as COVID-19.

Various embodiments provide an edible composition consisting of: cyanidin-3-glucosides is in a range from 2% to 6% by weight; andrographolides is in a range from 3% to 7% by weight; ascorbic acid is in a range from 9% to 13% by weight; beta glucans is in a range from 38% to 42% by weight; polysaccharides is in a range from 30% to 34% by weight; and at least one antioxidant is in a range from 6% to 10% by weight; wherein the edible composition is prepackaged in a capsule form.

Some embodiments provide a human edible composition, in the form of a single serving of one or more unit dosages, comprising 30-70 mgs of cyanidin-3-glucosides; 40-80 mgs of andrographolides; 75-125 mgs of ascorbic acid; 400-600 mgs of beta glucans; 300-500 mgs of polysaccharides; and 75-125 mgs of a blend of antioxidants.

Some embodiments provide a human edible composition, in the form of a single serving of one or more unit dosages, comprising: 5-100 mgs of cyanidin-3-glucosides; 10-200 mgs of andrographolides; 50-500 mgs of ascorbic acid; 100-1000 mgs of beta glucans; 100-1000 mgs of polysaccharides; and 50-500 mgs of a blend of antioxidants.

In some embodiments, a weight ratio of the cyanidin-3-glucosides to the andrographolides is in a range from 1:1 to 1:5. The cyanidin-3-glucosides can be extracted from black rice; the andrographolides can be extracted from *andrographis paniculata*; the beta glucans can be extracted from *agaricus blazei*; and the polysaccharides can be extracted from *coriolus versicolor*.

In some embodiments, the blend of antioxidants comprise: an extract of at least one of coffee, green tea, blackcurrant, blueberry, onion, apple, and acerola; and a concentrate of at least one of camu camu, quercetin, tomato, broccoli, acai, turmeric, garlic, basil, oregano, cinnamon, elderberry, carrot, mangosteen, sweet cherry, blackberry, chokeberry, raspberry, spinach, kale, bilberry, brussel sprouts, and broccoli sprout.

Various embodiments provide a method of increasing immunity to viral infections in human and animal patients, the method comprising administering to the patient the human edible composition.

Various embodiments provide. a composition in the form of tablets, wafer capsules, gel capsules, sticks, sachets, vials, droppers or in injectable form, the composition contains a mixture of: an extract of black rice; an extract of *andrographis paniculata*; ascorbic acid; an extract of *agaricus blazei*; an extract of *coriolus versicolor*; and at least one antioxidant.

Various embodiments provide a nutritional supplement in the form of tablets, wafer capsules, gel capsules, sticks, sachets, vials, droppers or in injectable form, the nutritional supplement comprising: a first composition consisting of: an extract of black rice; an extract of *andrographis paniculata*; ascorbic acid; an extract of *agaricus blazei*; an extract of *coriolus versicolor*; and at least one antioxidant; and a carrier.

In some embodiments, the extract of black rice comprises cyanidin-3-glucosides in the range of 5 to_100 mgs; the extract of *andrographis paniculata* comprises andrographolides in the range of 10 to 200 mgs; the ascorbic acid is in the range of 50 to 500 mgs; the extract of *agaricus blazei* comprises beta glucans in the range of 100 to 1000 mgs; the extract of *coriolus versicolor* comprising polysaccrides in the range of 100 to 1000 mgs; and the at least one antioxidant is in the range of 50 to 500 mgs.

Various embodiments provide an immune-enhancing composition in the form of tablets, wafer capsules, gel capsules, sticks, sachets, vials, droppers or in injectable form, the composition consists of: an extract of black rice comprising at least 25% by weight of cyanidin-3-glucosides; an extract of *andrographis paniculata* comprising at least 50% by weight of andrographolides; ascorbic acid; an extract of *agaricus blazei* comprising at least 50% by weight of beta glucans; an extract of *coriolus versicolor* comprising at 50% by weight polysaccharides; and at least one antioxidant.

The composition can have the weight ratio of the of cyanidin-3-glucosides to the andrographolides is in a range from 1:1 to 1:2. The composition can consist of the cyanidin-3-glucosides is in a range from 2% to 6% by weight; the andrographolides is in a range from 3% to 7% by weight; the ascorbic acid is in a range from 9% to 13% by weight; the beta glucans is in a range from 38% to 42% by weight; the polysaccharides is in a range from 30% to 34% by weight; and the at least one antioxidant is in a range from 6% to 10% by weight.

Some embodiments provide a method of increasing immunity to viral infections in human and animal patients The method can comprise administering to the patient the composition consisting of an extract of black rice comprising at least 25% by weight of cyanidin-3-glucosides; an extract of *andrographis paniculata* comprising at least 50% by weight of andrographolides; ascorbic acid; an extract of *agaricus blazei* comprising at least 50% by weight of beta glucans; an extract of *coriolus versicolor* comprising at 50% by weight polysaccharides; and at least one antioxidant.

Various embodiments provide an nutritional supplement consisting of: cyanidin-3-glucosides is in a range from 2% to 6% by weight; andrographolides is in a range from 3% to 7% by weight; ascorbic acid is in a range from 9% to 13% by weight; beta glucans is in a range from 38% to 42% by weight; polysaccharides is in a range from 30% to 34% by weight; and at least one antioxidant is in a range from 6% to 10% by weight; wherein the nutritional supplement is pre-packaged in a capsule form.

The nutritional supplement can consist of 30-70 mgs of cyanidin-3-glucosides; 40-80 mgs of andrographolides; 75-125 mgs of ascorbic acid; 400-600 mgs of beta glucans; 300-500 mgs of polysaccharides; and 75-125 mgs of a blend of antioxidants. In some configurations, the nutritional supplement can further comprise a capsule and a carrier.

The nutritional supplement can consist of: 5-100 mgs of cyanidin-3-glucosides; 10-200 mgs of andrographolides; 50-500 mgs of ascorbic acid; 100-1000 mgs of beta glucans; 100-1000 mgs of polysaccharides; 50-500 mgs of a blend of antioxidants; and the capsule.

The nutritional supplement can consist of: 5-100 mgs of cyanidin-3-glucosides; 10-200 mgs of andrographolides; 50-500 mgs of ascorbic acid; 100-1000 mgs of beta glucans; 100-1000 mgs of polysaccharides; 50-500 mgs of a blend of antioxidants; the capsule; and the carrier. The carrier can comprise a binder. The binder can be rice flour.

The weight ratio of the of cyanidin-3-glucosides to the andrographolides is in a range from 1:1 to 1:5. The blend of antioxidants can comprise: an extract of at least one of coffee, green tea, blackcurrant, blueberry, onion, apple, and acerola; and a concentrate of at least one of camu camu, quercetin, tomato, broccoli, acai, turmeric, garlic, basil, oregano, cinnamon, elderberry, carrot, mangosteen, sweet cherry, blackberry, chokeberry, raspberry, spinach, kale, bilberry, brussel sprouts, and broccoli sprout.

Various embodiments provide a method of increasing immunity to viral infections in human and animal patients, the method comprising administering to the patient the nutritional supplement consisting of: cyanidin-3-glucosides is in a range from 2% to 6% by weight; andrographolides is in a range from 3% to 7% by weight; ascorbic acid is in a range from 9% to 13% by weight; beta glucans is in a range from 38% to 42% by weight; polysaccharides is in a range from 30% to 34% by weight; and at least one antioxidant is in a range from 6% to 10% by weight; wherein the nutritional supplement is pre-packaged in a capsule form. The nutritional supplement can be in the form of tablets, wafer capsules, gel capsules, sticks, sachets, vials, droppers or in injectable form.

Various embodiments provide a method of increasing immunity to a virus in a subject. The method can comprise: administering to the subject one or more effective doses of an immune-enhancing natural-based composition; thereby stimulating increased expression one or more of IFN-γ, IL-1B, IL-6, IL-10, IL-12p40, IL-12p70, and TNF-α; inhibiting replication of the virus inside a cell of the subject, and preventing entry of virus into the cell.

The method of increasing immunity can further comprise increasing immunity to an upper respiratory tract viral infection. The upper respiratory tract viral infection can be COVID-19.

According to some aspects of the method of increasing immunity, the immune-enhancing natural-based composition comprises: cyanidin-3-glucosides in a range from 2% to 6% by weight; andrographolides in a range from 3% to 7% by weight; ascorbic acid is in a range from 9% to 13% by weight; beta glucans is in a range from 38% to 42% by weight; polysaccharides is in a range from 30% to 34% by weight; and at least one antioxidant is in a range from 6% to 10% by weight.

According to some aspects of the method of increasing immunity, the effective dose of the immune-enhancing natural-based composition comprises: 30-70 mgs of cyanidin-3-glucosides; 40-80 mgs of andrographolides; 75-125 mgs of ascorbic acid; 400-600 mgs of beta glucans; 300-500 mgs of polysaccharides; and 75-125 mgs of a blend of antioxidants.

Various embodiments provide methods of increasing immunity to viral infections in a human subject comprising: administering a nutritional supplement comprising an extract of black rice; an extract of *andrographis paniculata*; an extract of *agaricus blazei*; and an extract of *coriolus versicolor*.

In some embodiments, the nutritional supplement further comprises ascorbic acid. In some embodiments, the nutritional supplement further comprises at least one antioxidant The at least one antioxidant can comprise: an extract of at least one of coffee, green tea, blackcurrant, blueberry, onion, apple, and acerola; and a concentrate of at least one of camu camu, quercetin, tomato, broccoli, acai, turmeric, garlic, basil, oregano, cinnamon, elderberry, carrot, mangosteen, sweet cherry, blackberry, chokeberry, raspberry, spinach, kale, bilberry, brussel sprouts, and broccoli sprout.

The extract of black rice can comprise cyanidin-3-glucosides in the range of 5 to 100 mgs; the extract of *andrographis paniculata* can comprise andrographolides in the range of 10 to 200 mgs; the extract of *agaricus blazei* can comprise beta glucans in the range of 100-1000 mgs; the extract of *coriolus versicolor* can comprise polysaccrides in the range of 100 to 1000 mgs.

The extract of black rice can comprise cyanidin-3-glucosides in the range of 5 to 100 mgs; the extract of *andrographis paniculata* can comprise andrographolides in the range of 10 to 200 mgs; the extract of *agaricus blazei* can comprise beta glucans in the range of 100-1000 mgs; the extract of *coriolus versicolor* can comprise polysaccrides in the range of 100 to 1000 mgs; and the at least one antioxidant can be the ascorbic acid is in the range of 50 to 500 mgs and a blend of antioxidants can be in the range of 50 to 500 mgs.

Various modifications and changes may be made to an exemplary embodiment without departing from the scope of the present invention and all such modifications are intended to be included within the scope of the present invention.

In the foregoing description, the present invention has been described with reference to specific exemplary embodiments. The particular implementations shown and described are illustrative of the present invention and its best mode and are not intended to otherwise limit the scope of the present invention in any way. Indeed, for the sake of brevity, conventional manufacturing, connection, preparation, and other functional aspects of the method and system may not be described in detail. Furthermore, the connecting lines shown in the various figures are intended to represent exemplary functional relationships and/or steps between the various elements. Many alternative or additional functional relationships or physical connections may be present in a practical system.

It should be understood that steps within a method may be executed in different order without altering the principles of the present disclosure. For example, various embodiments may be described herein in terms of various functional components and processing steps. It should be appreciated that such components and steps may be realized by any number of hardware components configured to perform the specified functions.

Additionally, the components and/or elements recited in any apparatus embodiment may be assembled or otherwise operationally configured in a variety of permutations to produce substantially the same result as the present technology and are accordingly not limited to the specific configuration recited in the specific examples.

As used herein, the phrase "at least one of A, B, and C" can be construed to mean a logical (A or B or C), using a non-exclusive logical "or," however, can be contrasted to mean (A, B, and C), in addition, can be construed to mean (A and B) or (A and C) or (B and C). As used herein, the phrase "A, B and/or C" should be construed to mean (A, B, and C) or alternatively (A or B or C), using a non-exclusive logical "or."

The present invention has been described above with reference to various exemplary embodiments and examples, which are not intended to be limiting in describing the full scope of systems and methods of this invention. However, those skilled in the art will recognize that equivalent changes, modifications and variations of the embodiments, materials, systems, and methods may be made within the scope of the present invention, with substantially similar results, and are intended to be included within the scope of the present invention, as set forth in the following claims.

The invention claimed is:

1. An edible autoimmune inflammation modulating composition for improving immunity in a human, the composition comprising:
   *Oryza sativa* extract comprising cyanidin-3-glucoside in a range from 2% to 6% by weight of the composition;
   *Andrographis* paniculate comprising andrographolide in a range from 3% to 7% by weight of the composition;
   ascorbic acid in a range from 9% to 13% by weight of the composition;
   *Agaricus* blazei Murill comprising beta glucan in a range from 38% to 42% by weight of the composition;
   *Coriolus versicolor* comprising prebiotic polysaccharide in a range from 30% to 34% by weight of the composition; and
   an antioxidant mixture in a range from 6% to 10% by weight of the composition;
   wherein the weight ratio of the cyanidin-3-glucoside to the andrographolide is in a range from 1:1 to 1:2.

2. The edible autoimmune inflammation modulating composition of claim 1, wherein the
   a weight of the cyanidin-3-glucoside is in the range of 30 mg to 70 mg;
   a weight of the andrographolide is in the range of 40 mg to 80 mg;
   a weigh of the ascorbic acid is in the range of 75 mg to 125 mg;
   a weight of the beta glucan is in the range of 400 mg to 600 mg;
   a weight of the prebiotic polysaccharide is in the range of 300 mg to 500 mg; and
   a weight of the antioxidant mixture is in the range of 75 mg to 125 mg.

3. The edible autoimmune inflammation modulating composition of claim 1 further comprising a carrier and a capsule configured to encapsulate a mixture of the edible autoimmune inflammation modulating composition and the carrier.

4. The edible autoimmune inflammation modulating composition of claim 1, wherein:
   the cyanidin-3-glucoside is 25% of the weight of the *Oryza sativa* extract;
   the andrographolide is 50% of the weight of the *Andrographis* paniculate;
   the beta glucan is 50% of the weight of the *Agaricus* blazei Murill; and
   the prebiotic polysaccharide is 50% of the weight of the *Coriolus versicolor*.

5. The edible autoimmune inflammation modulating composition of claim 1, wherein:
   the cyanidin-3-glucoside is at least 25% of the weight of the *Oryza sativa* extract;
   the andrographolide is at least 50% of the weight of the *Andrographis* paniculate;
   the beta glucan is at least 50% of the weight of the *Agaricus* blazei Murill; and
   the prebiotic polysaccharide is at least 50% of the weight of the *Coriolus versicolor*.

6. The edible autoimmune inflammation modulating composition of claim 1, wherein the at least one antioxidant comprises:
   an extract of at least one of coffee, green tea, blackcurrant, blueberry, onion, apple, and acerola; and
   a concentrate of at least one of camu camu, quercetin, tomato, broccoli, acai, turmeric, garlic, basil, oregano, cinnamon, elderberry, carrot, mangosteen, sweet cherry, blackberry, chokeberry, raspberry, spinach, kale, bilberry, brussel sprouts, and broccoli sprout.

7. The autoimmune inflammation modulating composition of claim 1, wherein:
- the cyanidin-3-glucoside is about 2% by weight of the composition;
- the andrographolide is about 2.5% by weight of the composition;
- the ascorbic acid is about 7.5% by weight of the composition;
- the beta glucan a range is about 21% by weight of the composition;
- the polysaccharide is about 17% by weight of the composition; and
- the at least one antioxidant is about 8% by weight of the composition.

8. The edible autoimmune inflammation modulating composition of claim 7, wherein the at least one antioxidant comprises:
- an extract of at least one of coffee, green tea, blackcurrant, blueberry, onion, apple, and acerola; and
- a concentrate of at least one of camu camu, quercetin, tomato, broccoli, acai, turmeric, garlic, basil, oregano, cinnamon, elderberry, carrot, mangosteen, sweet cherry, blackberry, chokeberry, raspberry, spinach, kale, bilberry, brussel sprouts, and broccoli sprout.

* * * * *